US008329883B2

(12) United States Patent
Barale et al.

(10) Patent No.: US 8,329,883 B2
(45) Date of Patent: Dec. 11, 2012

(54) **METHODS FOR DETECTING VIRULENT *PLASMODIUM*, FOR EVALUATING *PLASMODIUM* VIRULENCE, AND FOR SCREENING NEW DRUGS EMPLOYING THE 3' UTR OF *PLASMODIUM* SUB2 AND THE *PLASMODIUM* SUB2 SERINE PROTEASE**

(75) Inventors: Jean-Christophe Barale, Paris (FR); Pierrick Uzureau, Wepion (BE); Catherine Braun-Breton, Montpellier (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 12/840,945

(22) Filed: Jul. 21, 2010

(65) Prior Publication Data

US 2011/0039262 A1 Feb. 17, 2011

Related U.S. Application Data

(62) Division of application No. 11/119,826, filed on May 3, 2005, now Pat. No. 8,012,706.

(51) Int. Cl.
*C07H 21/00* (2006.01)

(52) U.S. Cl. ...................................... 536/23.1; 536/24.1

(58) Field of Classification Search ........................ None
See application file for complete search history.

(56) References Cited

U.S. PATENT DOCUMENTS

2003/0229082 A1 12/2003 James et al.

FOREIGN PATENT DOCUMENTS

WO WO 9613607 A1 5/1996
WO WO 03057723 A2 7/2003

OTHER PUBLICATIONS

Liao et al. (Korean J. Parasitol., 48:291-295, 2010).*
Lewin (Genes IV, 1990, Oxford Univ. press, p. 806).
Howell et al., (J. Biol. Chem. 278, 23890-23898, 2003).
Uzureau et al. , (Cell. Microbiol., 6:65-78, Jan. 2004).
Lahue et al.. Yeast, 22:537-551, 2005.
Nakai et al., J. Biol. Chem., 268:24262-24269, 1993.
McDonald et al., Genetics, 171:901-911, 2005.
Green et al., Mol. Biochem. Parasitot., 150:114-117, 2006.
Barale et al., (PNAS, 96;6445-6450, 1999).
Michael J. Blackman, "Proteases in host cell invasion by the malaria parasite", Cellular Microbiology, vol. 6, No. 10, XP-002407195, Oct. 2004, pp. 893-903.
Fiona Hackett, et al., "PfSUB-2: A second subtilisin-like protein in *Plasmodium falciparum* merozoites", Molecular and Biochemical Parasitology, vol. 103, No. 2, XP-002407197, Oct. 15, 1999, pp. 183-195.
Vladimir Corredor, et al. "A SICAvar switching event in *Plasmodium knowlesi* is associated with the DNA rearrangement of conserved 3' non-coding sequences", Molecular & Biochemical Parasitology, vol. 138, No. 1, XP-004611799, Nov. 2004, pp. 37-49.
Vandana Thathy, et al., "Levels of circumsporozoite protein in the *Plasmodium* oocyst determine sporozoite morphology", The EMBO Journal, vol. 21, No. 7, XP-002407198, Apr. 2, 2002, pp. 1586-1596.
Karena L. Waller, et al., "Chloroquine Resistance Modulated in Vitro by Expression Levels of the *Plasmodium falciparum* Chloroquine Resistance Transporter.", The Journal of Biological Chemistry, vol. 278, No. 35. XP-002407199, Aug. 29, 2003, pp. 33593-33601.
International Search Report issued Nov. 28, 2006 in PCT/IB2006/001918.

* cited by examiner

*Primary Examiner* — Brian J Gangle
(74) *Attorney, Agent, or Firm* — Oblon, Spivak, McClelland, Maier & Neustadt, L.L.P.

(57) ABSTRACT

Methods for regulating the serine protease of *Plasmodium*. Recombinant DNA constructs which express the *Plasmodium* serine protease, especially those comprising a sub2 3'UTR and coding segment which express a SUB2 a serine protease. Recombinant *Plasmodium* containing such constructs and exhibiting increased virulence. Methods for detecting virulent *Plasmodium* strains by detecting the presence or amount of sub2 3'UTR sequences, sub2 mRNA or cDNA, SUB2 polypeptide expression, or other *Plasmodium* proteins, such as AMA1 or MSP1, which have been post-translationally modified by SUB2.

8 Claims, 16 Drawing Sheets

FIG. 3B

FIG. 6

SEQUENCE LISTING

```
<160> NUMBER OF SEQ ID NOS: 15

<210> SEQ ID NO 1
<211> LENGTH: 6
<212> TYPE: RNA
<213> ORGANISM: artificial
<220> FEATURE:
<221> NAME/KEY: misc_feature
<223> OTHER INFORMATION: Eukaryotic canonical site

<400> SEQUENCE: 1 aauaaa                                                              6

<210> SEQ ID NO 2
<211> LENGTH: 552
<212> TYPE: DNA
<213> ORGANISM: Plasmodium berghei
<220> FEATURE:
<221> NAME/KEY: misc_feature
<223> OTHER INFORMATION: sub2 3' UTR

<400> SEQUENCE: 2
```

```
tagatgattc catcgagaaa aggaggagat aatacattgt agaatctttg tgagacacat    60
tgatctcaca tatgagtata tatatctcca aaaatagta attaaaaaat tataatagtt   120
tttcctcaca atgatatagc ataatattgt tcatttattt ttttttattt tatgctttaa   180
taaattgttt ataaatattt ttttaatgta taatatgcat taaatgcata tttcgtattt   240
tttattttat atgtgtatgt atgactatat tttatattt gtatatagtt tgttttataa   300
aattatataa taaactttaa atataaacat taatatttg cctttcaaaa gcataaagcg   360
ttttaataag catgtttaat tatttagaga atatattatc ctttaataat attatcatta   420
tattaattta tccttataaa ttaaagtagt taaatgtagt ggaaaagttt agcaatttaa   480
ttcccataaa acatattgag gaataattac tgttgatttt tcataactta ttttattata   540
tatatgacta tt                                                      552

<210> SEQ ID NO 3
<211> LENGTH: 858
<212> TYPE: DNA
<213> ORGANISM: Plasmodium yoelii
<220> FEATURE:
<221> NAME/KEY: misc_feature
<223> OTHER INFORMATION: sub2 3' UTR

<400> SEQUENCE: 3
tagattattc caccgagaaa tgaggagaga atacattata gggttttttgt gagacacatt   60 gatctcacat atgagtatat attacacata tatttattta attatttgac attttcttaa   120
attttccttt ttttgtttta gaaatatat gtatatatat ctccaaaaaa tagtaattaa   180
aaaattataa tagttttttt tcacaatgat atagcataat attgttcatt tattttttct   240
attttttgct ttaataaatt gtttataaat atattttttt ttaatatata atatgcatta   300
aatgcatgtt tcgtcttttt tattttatat ccgtatgact atattttttat atttgtatat   360 agtttgtttt ataaaattac ataatcacct ttaaatattg gcattaatgc ttttcctttt   420
aaaagcataa agcgttttaa taaacatgtt taattattta gagaaatata ttaccctta   480 aaaatcatta tattaattta tactttataa attaaagtag ttaaattagc ggcaaattta   540
gcaatttaat tcttataaaa cattgaggaa taaaattgtt gatttttcat gacttatttt   600
atttatgacc tattttttat ttagtatgta ataaatacac ttttatacccc tcaaataaaa   660 ttttcttaca atttatttta tttatatatt tgtggaaaag aaaaatttaa cattaaaaaa   720
aatatatacg ctataaaaac tttataaata ttatttttga ataaatattt tattaaaagc   780
caaaaaataa aaaatatatc tataaaaaaa agccagataa aaatttttatt aattagctaa   840 ttttttttttt atcacaaa                                              858

<210> SEQ ID NO 4
<211> LENGTH: 850
<212> TYPE: DNA
<213> ORGANISM: Plasmodium falciparum
<220> FEATURE:
<221> NAME/KEY: misc_feature
<223> OTHER INFORMATION: Strain 3D7, sub2 3' UTR

<400> SEQUENCE: 4
tgatatataa aaaatatata acactttcag ttttatacac cttttttggaa tatatatata   60 tatatatttt catatttatt tattagtaaa taataaaaat taacccttttt atttttttaa   120 atattttctt tgttataaaa atatcatata tatttttta atttttatgt agcctattta   180
ttatatatat atatatatat ataatatata tatatatata tatatatatt tatgtatatt   240
```

-continued

```
ttattttta  atagtactca  tttttatgt  gaaaacacat  tatcctcttt  tttctgtttt    300
tcattttatt  ttatttatt  tatttattca  tttttttttt  ttggtataca  taatagcttt    360
tattagttcc  ataaatatgt  taaaaaaaaa  aaaatttaaa  acaagtgaca  tttaaacttg    420 atttatttt   taacctttca  aaaattaaat  ttatattatt  ttaaatatat  caaggaacta    480
taataatata  tgagaaaatt  tccaaatact  gataaaaaaa  aaatattacg  aaaaatattg    540
tttctaattt  ttttttacaa  aaataaaaaa  aaataagat   tatatatata  tatatatata    600
taatatagta  tatttatat   attaatttt   aatttctatt  aaataaagat  atatattata    660
actatataat  tatataagat  atatatattt  atatttaat   aaaaataaat  attaaataaa    720
atatcttctt  aaagttaata  tttatatatat  atgattttat  atataattat  ttacataatt   780
attattatcg  agtttatat   ttaatttatg  ttaagataaa  aaaaaaaaaa  aaaatatata   840
taacttttta                                                               850
```

<210> SEQ ID NO 5
<211> LENGTH: 27
<212> TYPE: DNA
<213> ORGANISM: artificial
<220> FEATURE:
<223> OTHER INFORMATION: Tun primer

<400> SEQUENCE: 5

```
tttttttttt tttttttttt acgacgt                                           27
```

<210> SEQ ID NO 6
<211> LENGTH: 31
<212> TYPE: DNA
<213> ORGANISM: artificial
<220> FEATURE:
<223> OTHER INFORMATION: primer

<400> SEQUENCE: 6

```
tttggatccc atcatcaaag taaacaacgc g                                      31
```

<210> SEQ ID NO 7
<211> LENGTH: 30
<212> TYPE: DNA
<213> ORGANISM: artificial
<220> FEATURE:
<223> OTHER INFORMATION: reverse primer

<400> SEQUENCE: 7

```
ccggatccat aaaaatatag tcatacatac                                        30
```

<210> SEQ ID NO 8
<211> LENGTH: 30
<212> TYPE: DNA
<213> ORGANISM: artificial
<220> FEATURE:
<223> OTHER INFORMATION: reverse primer

<400> SEQUENCE: 8

```
ccggatccat attatgctat atcattgtga                                        30
```

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9

-continued ttgggagaac aagcagttgg                    20

<210> SEQ ID NO 10
<211> LENGTH: 21
<212> TYPE: DNA
<213> ORGANISM: artificial
<220> FEATURE:
<223> OTHER INFORMATION: primer

<400> SEQUENCE: 10
gtaacctttc taagatcggc c                    21

<210> SEQ ID NO 11
<211> LENGTH: 4611
<212> TYPE: DNA
<213> ORGANISM: Plasmodium falciparum

<400> SEQUENCE: 11
cacgaggtct cgagtttttt tttttttttt ttgttatttt tttttttctc tttccgtata    60
atgctgaata ttatttatgt ggtttccttg atattaataa aatttatctt ttataaggaa   120
tgtaataata ataataataa ttatttaagt aatatagaat tatataatta taaactaagg   180
aagagaaaca ggattctaaa taataatata aatgatagga aatcctttttt gtctgattta   240
gaacaaaatt acaaaccatt atttgacata tatgagttat cagctaattt tgagaaaaga   300
agaaaagagt tagagaaaaa aacaaaggga gaagaaaatg aaatagaaaa aaaaaaggaa   360
aatgatttag aaaaaaaaaa agaaaatgat ttagaaaaag aatataatga tgtcataaat   420
ttattagaat taagtttaag ttctgaatat aaggaactaa atgccgatgt aagtaataat   480
gataattctg gacatgagga aaataataaa acacaaatta ataaaaaaaa ttcttcaaat   540
tataaaaatg ataaatctct tgatgaatta attaaaggcg caatacttaa attgaaacag   600
aatccaaata taaaaaataa aaatatgttg gattatgata aatatttaa aataattaaa   660
gaaaaattaa tcaataagaa tttggctagt aacaaaataa gggggggtga taatgaaaaa   720
ttaaaagagg aaaaaaaaca aagcgatata tcaacaaatg tagaagtcaa aaaagatatc   780
ataaatgatc aactaaataa aggtatacct acaagaaaag aaaataaaga tgatatgata   840
aataaagaaa gtaataagga ggatattact aatgaaggaa aatcgaattc tcttaataat   900
ttgaatacat taaataatga tggaaacata ataacaaaag tatatgacca ctatactata   960
gtaaccaatt ctaacgatat attaaatgat atttctattg atgcctcaga tatatcaaaa  1020
aatagtatag gaggtattaa tatccttttt aatgaaaacg ataatagtag ttttactcat  1080
cagagatata tagtactatc aaacaatgga gaaaaaaaat acaaaatagt tttaatgaca  1140
aagaatccta aatttatgga tatggatggt atatatgatg aagaagaaaa aaaagaatct  1200
cttattgaat taaatcaaaa ggtaaacaag gaggaaaata caaaccttta tgatggaacg  1260
gggacattat attatggtaa aaaatccaaa aaggaaaaag aaaatacaca acaaaaagga  1320
ggaaataatc caaatgtaga cataaacata ctcaacaata ataataataa taataataat  1380
aataacaata ataataatag taataataat agtaatagta tgaatgacga agaaatcaat  1440
tataataata ataataataa taaagaatca ccaagtatgt tcagacgttt tataaacttt  1500
ttaagtttct caggtaatga aaatgaaaca gaagatactt taatttatca taataaaaat  1560
gataattcct acaaaaataa aaaagaagga actggtaaaa ataatgataa taatgatcct  1620
aataataata ataataaaaa aattttgtta aatgttgata aacttgtaga tcaatatcta  1680
ttaaacttaa aaaataatca cacatcgaaa caggaattga tacttgtact taaaggagaa  1740

```
ttagatcttc attcgaaaaa tatgaaaaat gttacaaata atgcaaagaa aaatttagaa    1800
aaatatttta aagaacactt taaggaattc gataaaatat catatgatat atcaacaccc    1860
attaattttc tttgtatttt tataccaact gttttgata tgaataatat ggatttactt    1920
aaacaagcac tattaatatt acatagtgat ctacacgaat atgttgaaaa ttggagtttt    1980
tctagtacat accatacata cgaagcggat tatataaagg aacaagattc tgtgtatgat    2040
agatctccaa agaaaaata tataaaagcg agtaaaaat tatataacaa caaatattct     2100
tttttaaata aattcttaaa tattgaacca cttatattat ttgctaaaaa gttaaattca    2160
aaacgttcaa atattgagaa agaaatttta aattttttac ctaaggaatt aagagattat    2220
tccacatgga atttgtcaat tattagagtg ttcaatgcgt ggtttctggc tggatatggg    2280
aataagaatg taaaggtatg tgttgttgat tcaggggcag atataaatcg tgttgattta    2340
aatggtaatt tatatatacc agaatataat gaaaaatatg aaatgactca agatttttat    2400
aacttcatgg ttaaaaaatc ctacagatgc ttaggtcatg gatcacatgt cactggtatt    2460
ataggaggtg tagctaatga tttaggtgta gtaggtgtag ctcctaatat tacattaata    2520
tcattaagat ttattgatgg aaaaaatat ggtggaagtt ttcatgctat taaggcttta     2580
aatgtatgta tattaaataa agcaccaatt ataaatgcta gttggggctc tagtcatttt    2640
gacgttaatt tacatctgac tgtggagaga ttaaaatata cattaaatgg aaaggggagt    2700
gtgttaatag cagcatccgg aaataaaagt aacgataatg atatttcacc tttatacct   2760 gcaacattta catttcctca tgtttatagg taatacagaa tatgtataaa atatatgcaa    2820
gttggaaatg aattaatatg tatatatgga tatatatatg tatatatatg tatatatata    2880
tatatgttta ttttttttat ttttattttt ttatttttat tcttttttgt agtgtggcct    2940
ccattagcag aaattttgaa atttctccgt tctcaaatta tggatataag agtgtgcaca    3000
ttttagcccc aggtcatcac atatattcta ctattccaaa taactcatac aagatcttta    3060
caggtacttc tatggctgct cctcatgtat gtggtgtgag tgctttggta tattccgttt    3120
gttataacca aggttttatt cctcaagcgg aagaggtgtt agatatatta acaaggacat    3180
ctataaaaat aatttctaca aagaaaagaa ccataaatga cagtttagtt aatgcagaag    3240
gagcagtttt gactacttta ttaggaggac tatggatgca aatggattgt tattttgtta    3300
aatttaattt agaaaaaggc aagaaaaagc atattcctgt tgttttctcg gcttacaaga    3360
aaggagtata tgaaacagat atcgttatag ctattatacc tattgatggg aaatccaaaa    3420
tatatggaga aattcatatt cctataaaaa ttgtaaccga tgtaaatatt cccaatttcc    3480
aagaatctcc acgaagagga aaaaattata ctatagattc taatgaagca caacatgatg    3540
aagtcctttc ttatatctgt gaaaatgcct tatataattt gtatgaatat gatagtcatt    3600
atttgttggc ttctgtcata ttatttttc tagcattatt atccatattt gttggaatga    3660
tatatatgaa gtcgcgtaaa catagtgata agaaatgttc taaaaatctt atcaaaagta    3720
attatatacc agaaatggat gatggtatgg aagaaacaca acaactgcaa caagaaagaa    3780
gacaatattt cagagaatta tttggagaaa atttggaaaa gaattacgat cagcatttg     3840 tacaagattt tggtcaagat tttagacaag atttcaagct gggttcaaca ccagacttaa    3900
aacaatattc tgatatagat ttacaaaata agatacagca accggaaagg aaaaccgtaa    3960
agataattat taataacttt gaagatagaa agaaagagac cataagaaga ctactcaagg    4020
gattaaatta tgatggagaa aatgcaaaga aacatgattt cacgaatgaa agtattagca    4080
atagtaggaa aaattttaaa ttctcaaaca atacagaaat gaaaaaaaat actataaaaa    4140
```

| | |
|---|---|
| gtgaggacgt caaaatagca tctgacgata atgttaataa agcaatgaat caacttgatg | 4200 |
| atatgtttat gaaatgatat ataaaaaata tataacactt tcagttttat acaccttttt | 4260 |
| ggaatatata tatatatata ttttcatatt tatttattag taaataataa aattacccct | 4320 |
| ttatttttt aaatattttc tttgttataa aatatcatat atattttttt aattttatg | 4380 |
| tagcctattt attatatata tatatatata taaatatat atatatat atatatat | 4440 |
| ttatgtatat tttatttttt aatagtactc attttttatg tgaaaacaca ttatcctctt | 4500 |
| ttttctgttt tcattttat tttattttat ttatttattc atttttttt tttggtatac | 4560 |
| ataatagctt ttattagttc cataaaatagt gttaaaaaaa aaaaaaaaa a | 4611 |

<210> SEQ ID NO 12
<211> LENGTH: 3678
<212> TYPE: DNA
<213> ORGANISM: Plasmodium yoelii

<400> SEQUENCE: 12

| | |
|---|---|
| atgttgagaa cattttatgt tctatcctta atgctaattg aatttatact gcacaagggt | 60 |
| cagtataata agcatatttg ttcaaaaaat ttgaaaaaat ataattttgt tggtaagaaa | 120 |
| catcgaattt tggcaagtat tattgaagat agggaaaaac aagttgaaga tataacagat | 180 |
| ggttataagc ctatatttaa catttatgaa atatctgcag catttcacaa aaaaaaagat | 240 |
| atagcagata aaaaaaaaag acgaagatac ggaaaccaac aaagtataga aaacagaaga | 300 |
| attgctgaag aaaatgaaag acgtctatca aatcaattgg atgatataca atttattgaa | 360 |
| ttatctaata aatatcctaa tataggaaaa caaaattctc aacaaaataa agtaaataaa | 420 |
| ataaataatc aaaatggtgc atcgaattca atgataata taagaaatga tgaggatgag | 480 |
| gatgagggtg aggatgaaga tgaagatgat gatttgatag aaggcaggaa agataattta | 540 |
| gaagaggatg atttagtaga aaaaaatggt gccaatttaa aaaggggggaa catgcatgga | 600 |
| caggaagaaa aaaataaaaa tataaacaca actccaggca atgagaataa tagcaaaaat | 660 |
| gtaaatgata taaaaaaag tggtataagt ctaaaagata aaattgacaa taatgagcaa | 720 |
| cataatagtg gtttaaaagg cacgacgaaa tatttagatg ataatataaa aacatataca | 780 |
| tttgaccatt ataaacttat aacaaattct gataatatat taaatgatat aaaagtagat | 840 |
| gcatcagata tttcaaagct aagtataaat agcttaagta tagaatataa tgaagtaaat | 900 |
| aaaaccgaat acacacacca aaggcatata gtattaacta ataaaggaaa tagacgatat | 960 |
| aaaatatttc taatgacaaa aaatccaaag tttacgaaaa cagaggatat tgaagaacct | 1020 |
| gaaatgagtt ttattcaaac agaaacagga gagaatacaa atgaaaaaga agacgaggaa | 1080 |
| aactatttga tgaaaatttt gtatagtgga tttgggacta ttgattatga aaatggttat | 1140 |
| tcaaaaaaaa aaaaaaaaat taacagtgaa cacgcaagtg aacttaatga taaaattagt | 1200 |
| aacagccaaa acattgaaaa aagtgattct catgaaaatg aaaaatataa tcatggattt | 1260 |
| atagggaaga tacaaagttt ttttagtttt ttatccatcc caagtagcaa gaaagatgat | 1320 |
| agtattggaa gtgaaaaaaa atctgaggaa aggaacaatg tcgattctaa acctaaatta | 1380 |
| aataagaaac ctaatgatac ggccaaaaaa aataattcaa ataaaatttt gactgtagac | 1440 |
| aaagttacag atcaatatct attaaactta agaataaaaa atatgaaaga caagaattg | 1500 |
| atattcattt tccatgggga tttagattta cattcgaaga agatgaaaac aattataaat | 1560 |
| gaagcaaatg ttaaatttac aaaatatata aatatgcatt ttaaagacgt taagaatata | 1620 |
| cgttatgata tatcatcacc aataaacttt gtgtgttttt ttattcctat aattttgat | 1680 |

```
atgagcaatt taaagatatt aaaagaggca ttaattatat tgcataatga gctcaagaat    1740
tatatcgata attggaattt ttcaaatact tatatagcat ttgataccga ttatgaaaat    1800
gaagatattg acaatgcaat gaataaatta atgaaaata tgaaaaaata tattaaaaaa    1860
cccaaaaaat tatataatat aaaatattca ttttttaagaa aaatgtgggg tctagaatca   1920
attttctctt tatccaaaaa tcgaaatcaa aaaatgctg gaatagaaga aaaaattttg    1980
aacgcattac caaaagaatt gaaagagtat tcgacttgga atttatcttt tataagagta   2040
tttaatgctt ggcttttgtc tgggtatgga aataaaatg taaagatatg tgttatagat    2100 tcagggttg ataaaaacca tatagattta gcaaaaaata tatacacacc gaaatattca    2160
gatagatatg aaatgacaga tgattttttt gattttatgg ttaaaaatcc aatagataca   2220
tctgggcatg gtacacatgt ttctggaata gcagctgctt cggcaaattc tttaggtatg   2280
gttggtgttg ctcctgatgt caatttgata tctttacgat ttattgatgg agatagttat   2340
ggaggtagtt tccatgtaat taaagctata atgtttgta tattaaacaa atcgccaatt    2400
attaatgcta gttggggttc tagaaattat gatacgaata tgttcttagc tattgaaaga   2460
ttaaaatata cttttaaggg gaaaggaaca gttttttatag ctgcagcagg aaatgaaaat   2520
aaaaacaacg atctttatcc tatataccct gctagttata aacttccaaa tgtttatagt   2580
gttggttcca tcaacaaatt cttacaaatt tcaccatttt ctaattatgg agctaacagt   2640
gtgcacattc ttgcaccagg acatcacata tattccacaa cacctatgaa cacatacaaa   2700
atgaatacag gtacttctat ggcagcccct catgtatcgg gagtagctgg attgatatat   2760
tcggtatgtc ataaacaagg atttatacct gaatctgatg aagttttaga tataataaca   2820
aggacatcta taaaaatagt atctaaggac aaaaaaacaa tacataatag tttaataaat    2880
gcagaagcag cagtattaac tacattactg ggaggtttat ggatgcaaat ggattgccat   2940
tttgctaagt tttatttaaa taaagatcaa caaaaaaaca ttcctgttgt attttcagca   3000
tataaagatg gaatgtatga atcagatata attataggaa ttcaacctga agattctaat   3060
tcaaaagaat atggagaaat tgtgattcct attaaaatat taacaaatcc caaattaaaa   3120
aattttaatt tatcaccaag agttggaaaa aaaatccaca ttgatgcaaa tgagtcaaat   3180
gatgatatat tatcatacat ttgtgaaaat gctttatata atttatatga gcatgacaac   3240
agttttttaa tttcatcatt gatattgttc tttataggaa ttatattaat cgctttagca   3300
tcgattgtgt ttttttttaaa acatcatcaa agtaaacaac gagatgccga aaaatatatg   3360
catcaaaaaa tggtagatag ggcacatgga ataaaatata attttaagga tgcgggtgcc   3420
gatggtatta aaagaataaa tacaatggat gacaatataa acaatcaccg aaatactcag   3480
agatttacta ttgttcaaaa tgaagataat atgtatgtgc taaaaaaaaa aagttctatt   3540
caagcaaaat atgaaccacg caatgaattg gtaaaacgcc cacttgtaaa acgtccaatt   3600
gtaaagcatg cagatataaa tgtaaatttc aaaaatatag atgaattata cgaaccacaa   3660
aacaactcac cggaatag                                                   3678
```

<210> SEQ ID NO 13
<211> LENGTH: 552
<212> TYPE: DNA
<213> ORGANISM: Plasmodium berghei
<220> FEATURE:
<221> NAME/KEY: misc_feature
<223> OTHER INFORMATION: Pbsub2-3'UTR

<400> SEQUENCE: 13

```
tagatgattc catcgagaaa aggaggagat aatacattgt agaatctttg tgagacacat     60
tgatctcaca tatgagtata tatatctcca aaaaatagta attaaaaaat tataatagtt    120
tttcctcaca atgatatagc ataatattgt tcatttattt ttttttattt tatgctttaa    180
taaattgttt ataaatattt ttttaatgta taatatgcat taaatgcata tttcgtattt    240
tttattttat atgtgtatgt atgactatat tttatatttt gtatatagtt tgttttataa    300
aattatataa taaactttaa atataaacat taatatttg cctttcaaaa gcataaagcg     360
ttttaataag catgtttaat tatttagaga atatattatc ctttaataat attatcatta    420
tattaattta tccttataaa ttaaagtagt taaatgtagt ggaaaagttt agcaatttaa    480
ttcccataaa acatattgag gaataattac tgttgatttt tcataactta ttttattata    540
tatatgacta tt                                                         552
```

```
<210> SEQ ID NO 14
<211> LENGTH: 623
<212> TYPE: DNA
<213> ORGANISM: Plasmodium yoelii
<220> FEATURE:
<221> NAME/KEY: misc_feature
<223> OTHER INFORMATION: Pysub2-3'UTR

<400> SEQUENCE: 14
tagattattc caccgagaaa tgaggagaga atacattata gggttttgt gagacacatt     60 gatctcacat atgagtatat attacacata tatttattta attatttgac attttcttaa    120
attttccttt ttttgtttta gaaaatatat gtatatatat ctccaaaaaa tagtaattaa    180
aaaattataa tagtttttt tcacaatgat atagcataat attgttcatt tatttttct     240 attttttgct ttaataaatt gtttataaat atattttttt ttaatatata atatgcatta    300
aatgcatgtt tcgtcttttt tatttatat ccgtatgact atattttat atttgtatat     360 agtttgtttt ataaaattac ataatcacct ttaaatattg gcattaatgc ttttcctttt    420
aaaagcataa agcgttttaa taaacatgtt taattattta gagaaatata ttacccttta    480
aaaatcatta tattaattta tactttataa attaaagtag ttaaattagc ggcaaattta    540
gcaatttaat tcttataaaa cattgaggaa taaaattgtt gattttcat gacttatttt     600 atttatgacc tattttttat tta                                             623
```

```
<210> SEQ ID NO 15
<211> LENGTH: 635
<212> TYPE: DNA
<213> ORGANISM: Plasmodium falciparum
<220> FEATURE:
<221> NAME/KEY: misc_feature
<223> OTHER INFORMATION: Pfsub2-3'UTR

<400> SEQUENCE: 15
tgatatataa aaatatata acactttcag ttttatacac ctttttggaa tatatatata     60
tatatatttt catatttatt tattagtaaa taataaaaat taacccttttt atttttttaa   120 atattttctt tgttataaaa atatcatata tattttttta atttttatgt agcctattta    180
ttatatatat atatatatat ataatatata tatatatata tatatatatt tatgtatatt    240
ttatttttta atagtactca ttttttatgt gaaaacacat tatcctcttt tttctgtttt    300
tcattttatt ttattttatt tatttattca ttttttttt ttggtataca taatagctttt    360 tattagttcc ataaatatgt taaaaaaaaa aaaatttaaa acaagtgaca tttaaacttg    420
atttattttt taaccttttca aaaattaaat ttatattatt ttaaatatat caaggaacta   480
```

```
taataatata tgagaaaatt tccaaatact gataaaaaaa aaatattacg aaaaatattg        540
tttctaattt tttttacaa aataaaaaa aaaataagat tatatatata tatatatata        600
taatatagta tattttatat attaatttt aattt                                  635
```

METHODS FOR DETECTING VIRULENT *PLASMODIUM*, FOR EVALUATING *PLASMODIUM* VIRULENCE, AND FOR SCREENING NEW DRUGS EMPLOYING THE 3' UTR OF *PLASMODIUM* SUB2 AND THE *PLASMODIUM* SUB2 SERINE PROTEASE

REFERENCE TO SEQUENCE LISTING

This application contains a sequence listing which forms a part of the disclosure.

BACKGROUND OF THE INVENTION

1. Field of the Invention

The invention pertains to recombinant *Plasmodium* expressing the SUB2 subtilisin-like protease which has a modified non-coding 3'UTR (3 prime untranslated region). The invention also related to methods for identifying virulent strains, and/or evaluating the virulence, of *Plasmodium*, and for screening new anti-malaria drugs are disclosed.

2. Description of the Related Art

*Plasmodium* is the parasite that causes malaria. The host-parasite relationship between malaria and its host involves a complex equilibrium between parasite multiplication, which is essential for its dissemination, and host responses[1]. Collateral damage attributable to the host-parasite interaction is responsible for the disease burden, morbidity and mortality in endemic areas where malaria is a major public health problem[2].

The virulence of malaria is associated with the multiplication rate of the parasite and the ability of *Plasmodium* blood states to cytoadhere microvessels in deep organs[1,3,4]. While virulence factors involved in cytoadherence have been identified[4], those involved in high multiplication rate, for which erythrocyte invasion by merozoite is a crucial step, remain poorly understood[1,3,4].

Proteases are known to play a crucial role in various infectious diseases and cancer and have been successfully defined as chemotherapeutic targets. The specificity of protease activity permits the design of highly specific inhibitors which block a pathogenic process without considerable toxic side effects. Thus protease inhibitors are selectively toxic agents applicable for therapeutic use.

Biochemical and genetic analysis have shown that proteases and particularly serine proteases play a central role for the liberation and entry of merozoites into the host red blood cell.

Compared to intra-erythrocytic parasite states, the merozoite, as the sporozoite, is briefly free in the host plasma and therefore accessible to external factors including host immune factors like antibodies or to therapeutic drugs. The Merozoite Surface Protein 1 (MSP1) of *Plasmodium* is considered a promising candidate for a malaria vaccine. MSP1 undergoes a two step maturation process. The final processing of MSP1-42 occurs while the merozoite enters into the host RBC and is achieved by a parasite membrane-bound and calcium-dependent serine protease. Despite MSP1 polymorphism, this sequential processing is precisely conserved, even amongst different *Plasmodium* species. Even if the biological function linked to this maturation is still unknown, its inhibition using specific monoclonal antibodies or serine protease inhibitors efficiently blocks the RBC invasion.

It has recently been shown that the same parasite serine-protease is responsible for the second maturation step of the vaccine candidate Apical Membrane Antigen-1 (AMA1). Originally, AMA1 was identified to be the target of monoclonal antibodies which prevent RBC invasion by merozoites and more recently hepatocyte invasion by sporozoites. The inhibition of the maturation of AMA1 results in abortive RBC or hepatocyte invasion by the merozoites and the sporozoites, respectively.

Over the last decade, the establishment of *Plasmodium* genetic tools[7], the genome sequencing of the laboratory clone *P. falciparum* 3D7[8] and various parasite transcriptome and proteome global projects[9,10], have made profound changes in the field of malaria research. Interestingly, global expression profiling shows that 50% of the 5400 parasite genes are stage regulated, while the proportion of proteins predicted to be involved in gene regulation is low, especially when compared to *S. cerevisiae*[8]. Only a handful of regulatory elements have been identified[11,12] and none is known that controls the multigene family coding for proteins mediating cytoadherence, which are subjected to antigenic variation.

A regulatory role for the respective introns of some malaria genes and 3'UTR (3 prime untranslated region) has been recently proposed[13], as previously shown for the 3'UTR of the ookinete Pgs28 gene[14]. The 3'UTR, and particularly the addition of a polyadenylated tail, have been widely shown to play a central role in the regulation of eukaryotic[15] and prokaryotic[16] gene expression via the modulation of messenger RNA (mRNA) stability and translation initiation.

In malaria parasites, poly-A addition does not necessarily occur at the eukaryotic canonical AAUAAA (SEQ ID NO: 1) site and poly-$A^-$ mRNA have been identified[17,18]. In the absence of an inducible system to genetically study essential malaria genes, the deletion of 3'UTR was used to decrease gene expression, revealing interpretable phenotypes[19,20]. To evaluate in vivo the contribution of the crucial merozoite subtilisin-like *P. berghei*-SUB2 protease[5,6] to the parasite life cycle, the inventors aimed to modulate Pbsub2 expression via the modification of its 3'UTR.

BRIEF DESCRIPTION OF THE INVENTION

The inventors have now demonstrated that efficient expression of the essential merozoite subtilisin-like maturase SUB2 strictly depends on functional poly-A sites, whose mutation gives rise to recombinant parasites over-expressing SUB2. The accumulation of SUB2 in these recombinant parasites correlates with more efficient maturation of the surface antigens MSP1 and AMA1, which are both vaccine candidates, and increased virulence of these recombinant *Plasmodium* organisms. The inventors thus show that non-coding regions involved in the regulation of crucial genes can be important virulence factors. Such genes may represent a dormant reservoir of virulence in *Plasmodium* and in other parasitic organisms in which invasion or virulence is mediated by enzymes involved in polypeptide/antigen maturation, such as the particular polypeptides/antigens which mediate host cell adhesion or invasion. Such parasitic organisms include *Toxoplasma, Babesia, Leishmania* and *Trypanosomes.*

For the first time, the inventors have now demonstrated that SUB2 is involved in the maturation of the merozoite surface vaccine candidates MSP1-42 and AMA1 and have shown that these maturations are not only crucial for the host cell invasion to succeed, but represent a limiting step on virulence in vivo. Based on these discoveries defining SUB2 as a maturase whose activity is critical for the biological cycle of malaria parasites, they establish that SUB2 is an anti-malaria drug target.

The inventors have discovered that the efficient expression of the essential merozoite subtilisin-like maturase *P. berghei*-SUB2[5,6] strictly depends on functional poly-A sites, the mutation of which gives rise to malaria parasites which overexpress PbSUB2. A significantly higher parasite multiplication rate in vivo correlates with the accumulation of PbSUB2 since higher amounts of this enzyme provide a more efficient maturation of merozoite surface proteins, such as MSP1 (Merozoite Surface Protein 1) and AMA1 (Apical Merozoite Antigen 1), which are both candidate antigens for vaccine production.

Host cell invasiveness is known to be a key factor of malaria parasite virulence[1] which aggravates when the parasite does not show any selectivity for blood cells[3,23]. Beyond the first direct evidence that SUB2 is involved in the maturation of the merozoite surface vaccine-candidates MSP1-42 and AMA1, the present inventors genetically demonstrate that this maturation is not only crucial for the host cell invasion to succeed, thus confirming previous biochemical and immunological studies[21,24], but is also a limiting step in vivo. These discoveries indicate that in vivo, maturation of these proteins contributes to the invasion of host blood cells in an age-independent manner. The present inventors have thus defined SUB2 as a potent malaria virulence factor related to tropism independent host-cells invasion.

Based on these discoveries the present inventors describe new methods for determining and/or evaluating parasite virulence based on the presence of particular motifs in non-coding region sequences, such as a motif found in the 3' UTR of sub2. The 3' UTR or 3 prime untranslated region corresponds to a section of mRNA that is past the stop codon for a coding region or exon. Graphically it may be depicted as follows: 5'-UTR—translated RNA—3'UTR.

Since regulation of sub2 gene expression has now been demonstrated to be an important virulence factor, methods of determining and/or evaluating and/or quantifying virulence may be based on the identification of regulatory sequences in the 3' UTR, the amount of sub2 mRNA (or cDNA corresponding to this mRNA), the amount of SUB2 protein expressed, or on SUB2 activity, for example, as measured by the post-translational processing of AMA1 or MSP1 polypeptides.

Increased or decreased virulence of a modified organism is based on a comparison with the virulence of corresponding unmodified organism or control strain. Likewise, the term "attenuated" means less virulent when compared to the corresponding unmodified or control strain.

BRIEF DESCRIPTION OF THE DRAWINGS

FIG. 1: Pbsub2 3'UTR characterization and modification following a double crossing-over strategy.

FIG. 1A. Pbsub2 specific 3'RACE was performed on *P. berghei* segmented schizonts total RNA, fractionated on a 1.5% agarose gel, ethidium bromide stained (Lane 1) or Southern-blotted and probed with Sub2Cter (Lane 2). Lanes 3, 4 and 5 correspond to RT-PCR performed respectively without reverse transcriptase, on genomic DNA and without template. Size markers are indicated. Polyadenylation signals and CA addition sites of the Pbsub2 3'UTR are schematised on the left panel. The position of the nucleotides is relative to the Pbsub2 start codon. In FIG. 1A, the two polynucleotide sequences at the top correspond respectively to SEQ ID NO: 2 nucleotides 306-317 and 343-374 and the two polynucleotide sequences at the bottom correspond to SEQ ID NO: 2 nucleotides 176-187 and 215-231.

FIG. 1B. Schematic representation of the wild type Pbsub2 3'UTR double crossing-over modification strategy and (bottom) the resulting WT-TmDX, single (SPA) or null poly-A sites (NPA) recombinant loci.

The polyadenylation sites (•), the TrimycDuoXpress (TmDX) epitope (hatched box) and the homologous coding (shaded) and untranslated (thickened) regions are indicated. The position of the BsmI (B), ClaI (C), HindIII (H) and SacI (S) restriction sites are indicated.

FIG. 1C. Genomic DNA prepared from WT-TmDX (w.) and SPA-TmDX (S.) cloned parasites was digested as indicated and probed with Sub2Cter or TgDhfr specific probes. The pattern obtained for SPA-TmDX gDNA supports a 0.2 kb truncation of the wild-type Pbsub2 3'UTR (FIG. 1C). Size markers are indicated.

FIG. 2: Comparative analysis of the Pbsub2 mRNA and protein in WT-TmDX1 and SPA-TmDX1 recombinant parasites.

FIG. 2A. Northern blot analyses were performed on total RNA extracted from wild type and recombinant parasites, fractionated and probed with Sub2Cter (upper panels) or Pbrab6 (lower panel) specific probes.

FIG. 2B. Western blot analysis of proteins SDS-extracted from segmented schizonts using anti-c-myc and trans-species specific anti-Plasmodium HSP70 specific monoclonal antibodies.

FIG. 2C. Subcellular localisation of the tagged PbSUB2 protein. Immunofluorescence analyses were performed on air-dried segmented schizonts, incubated with Sub2Cter-GST serum or the anti-c-myc plus the anti-Xpress monoclonal antibodies. Nucleus staining (Propidium Iodide, red) is merged with the antibody labelling (FITC, green).

FIG. 3: Comparative analysis of PbMSP1-42 and PbAMA1 maturation in WT-TmDX1 versus SPA-TmDX1 recombinant parasites.

Western blot analyses of SDS-extracted proteins from mature merozoites using rabbit anti-PbMSP1 polyclonal serum, rat trans-species specific anti-AMA1/28G2 (C) and mouse HSP70/1-C11 (B, D) specific monoclonal antibodies. The equivalent number of parasites per lane, and molecular weight markers are indicated.

FIG. 4: In vivo multiplication rates of the WT-TmDX1 versus SPA-TmDX1 in Balb/c and C57B1/6 mice.

Four BALB/cJ (A panel) or five C57B1/6J mice (B panel) were infected with $5\times10^4$ WT-TmDX1 (triangle) or SPA-TmDX1 parasites (square). Parasitaemia monitored using Giemsa stained blood smears are presented from day 2 to day 6 post-injection (dpi). The percentage of WT-TmDX1 (open triangle) or SPA-TmDX1 (open square) parasites in reticulocytes is presented with broken lines on the right panel. Values represents mean±SD of 4-5 mice per group, $p<0.05$ versus WT-TmDX1 as calculated by Mann Whitney U-test.

FIG. 5: Chromosomal localisation of the Pbsub2 recombinant loci.

The *P. berghei* chromosomes were prepared from wild type, SPA-TmDX and five WT-TmDX clones and separated by CHEF. Chromosomes 9 to 12 are indicated.

FIG. 5A. The wild type, WT-TmDX1 and SPA-TmDX1 *P. berghei* chromosomes were probed with Sub2Cter specific probe.

FIG. 5B. The wild type, SPA-TmDX1 and WT-TmDX1, 2, 4, 6 and 7 chromosomes were probed with TgDhfr specific probe. Given the unexpected rearrangement of the chromosome bearing Pbsub2 in the WT-TmDX2 clone, further analyses were performed with WT-TmDX1.

FIG. 6. Alignment of the 3'UTR of Pbsub2, Pysub2 and Pfsub2. In FIG. 6, Pbsub2-3'UTR, Pysub2-3'UTR and Pfsub2-3D7-3'UTR respectively correspond to SEQ ID NOS: 2, 3 and 4. Consesus nucleotides shared by the depicted sequences appear with a black background.

The sequences corresponding to the 3'UTR of Pfsub2-3D7 and Pysub2, were extracted from www.plasmodb.org, and aligned with Pbsub2 (Genebank access number AJ242629) using CLUSTALW (Thompson, J. D., Higgins, D. G. and Gibson, T. J. (1994). Nucleic Acids Research, 22:4673-4680). Identical residues appear in a black background and the stop codon of each gene is boxed. "AAUAAA" (SEQ ID NO: 1) poly-adenylation signals and "CA" dinucleotides corresponding to the poly-A tail addition sites are labelled respectively in red and blue. Distal and proximal Pbsub2 "AAUAAA" (SEQ ID NO: 1) poly-adenylation signals described in this issue are indicated. Pfsub2 and Pysub2 putative "AAUAAA" (SEQ ID NO: 1) poly-adenylation signals and "CA" poly-A tail addition sites have been identified using www._softberry.com/cgi-bin/programs/polyah.pl and http://_rulai.cshl.org/sgi-bin/tools/polyadq online software.

Figure 3A:
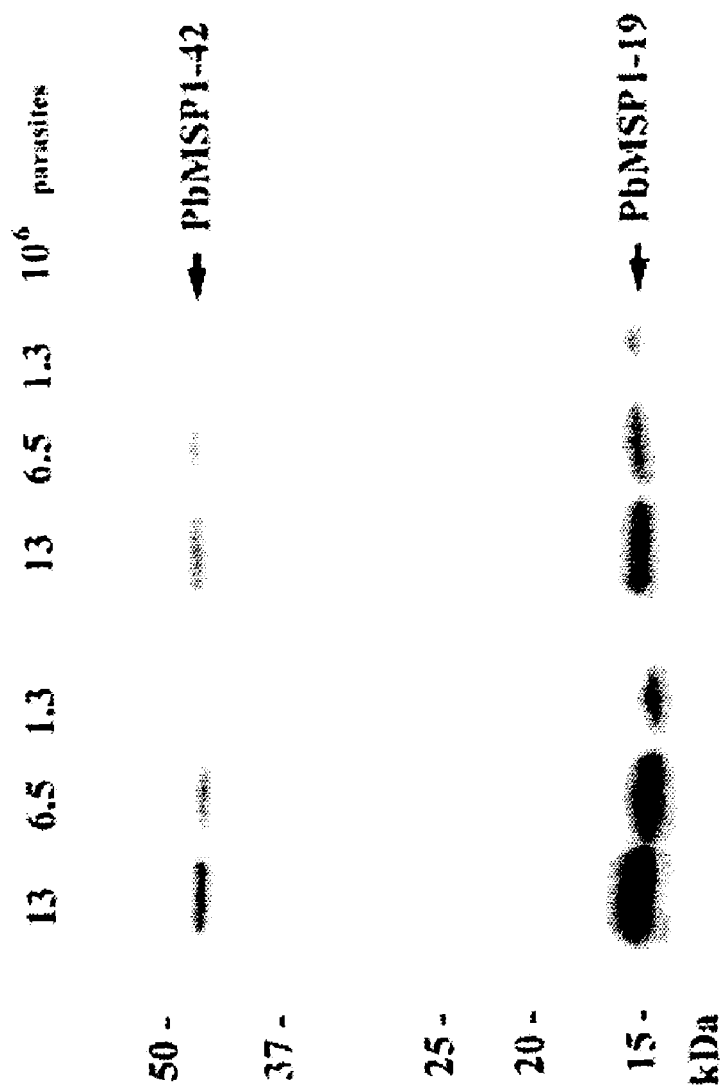
Figure 3C:
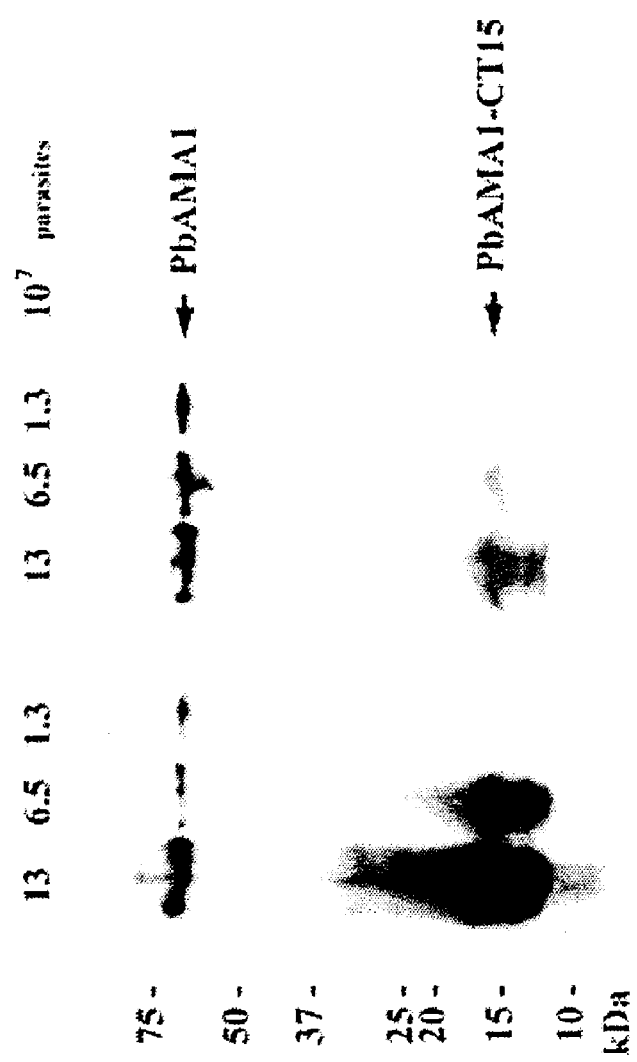
Figure 3D:
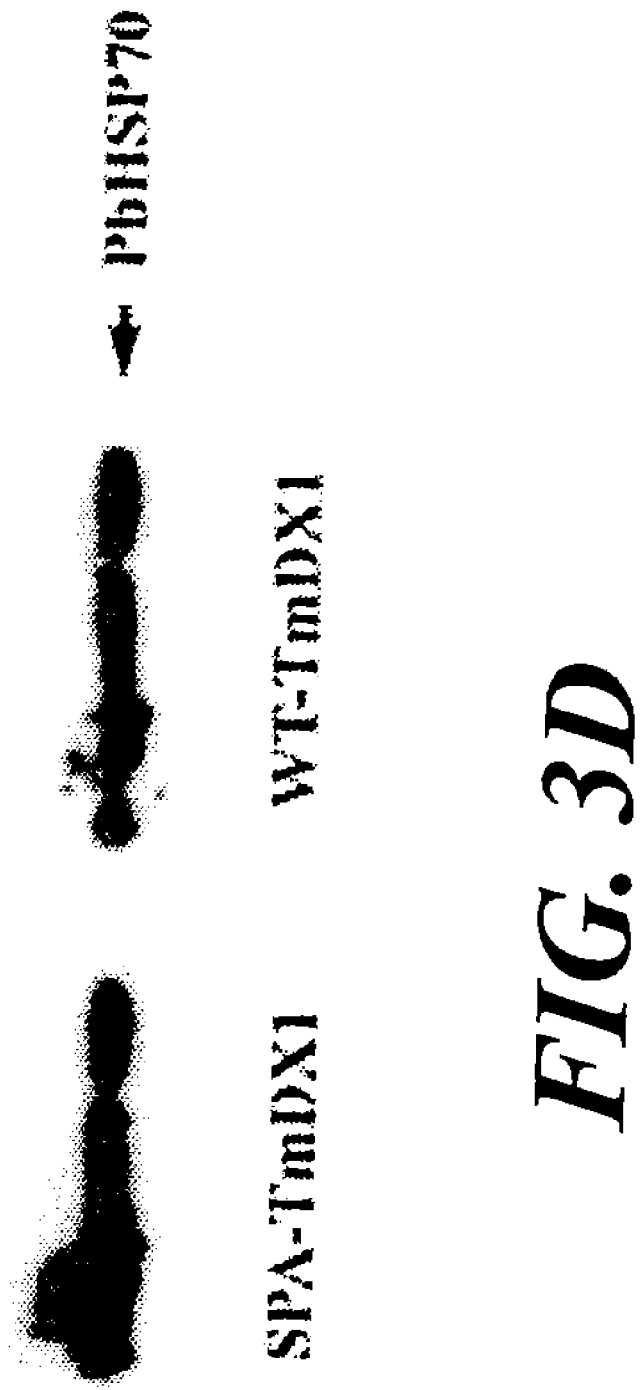
Figure 7:
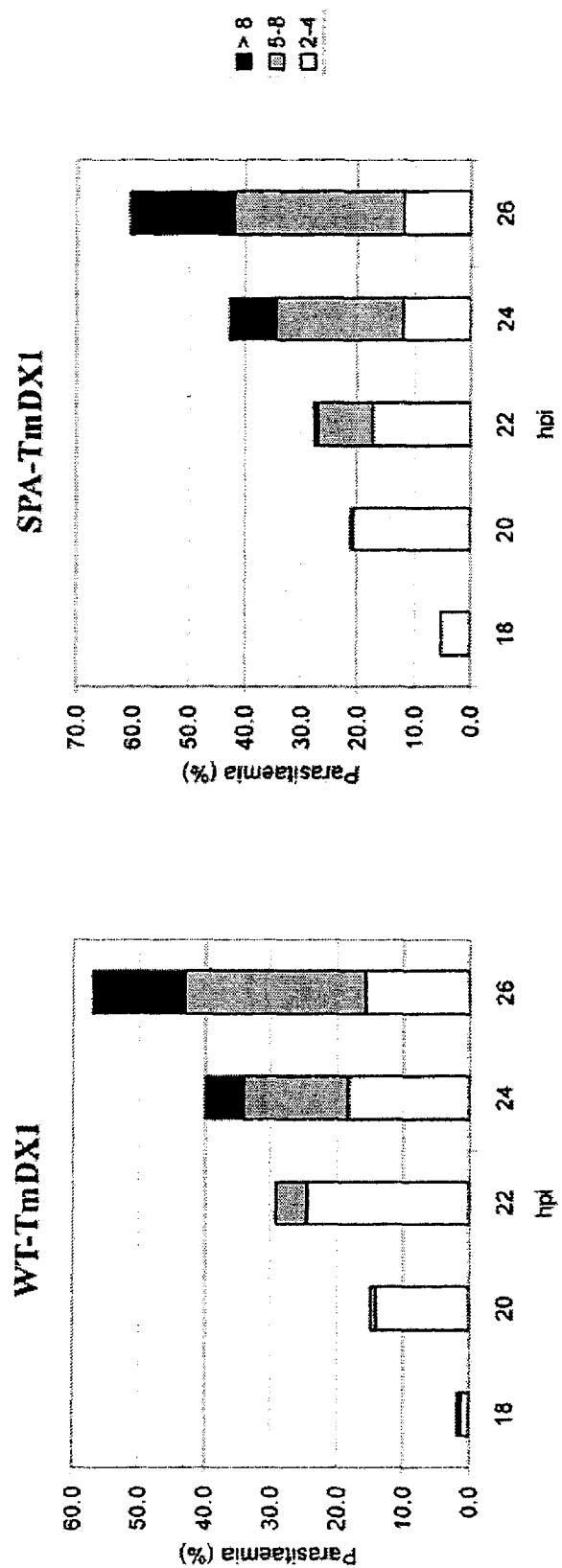
Figure 3B:
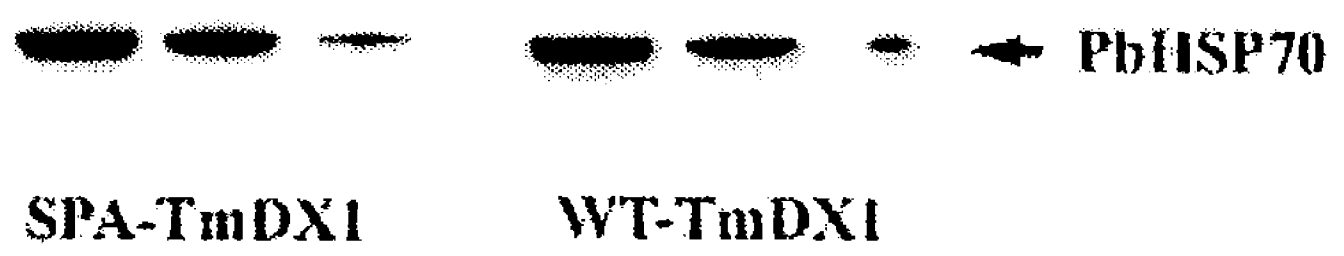

FIG. 7 (Supplemental FIG. 3). Measure of the erythrocytic cycle length of WT-TmDX1 and SPA-TmDX1 parasites in vitro.

The WT-TmDX1 and SPA-TmDX1 parasites were synchronised by inoculation of mice with merozoites. The parasites collected 4 hours later were in vitro cultured for 26 hours post-invasion (hpi). The percentage of emerging parasites with 2 to 4 (plain line), 5 to 8 (broken line), and more than 8 nuclei (dots) has been determined every two hours from 18 to 26 hpi, Determination of the in vitro schizogony properties. The synchronised WT-TmDX1 or SPA-TmDX1 parasites were prepared as follow: ten Swiss mice were infected with $2.5 \times 10^7$ parasites on day 0. Two days later, the blood was collected by heart puncture and maturated in vitro as previously described (van Dijk et al. (1995), Science 268, 1358-62). Merozoites were collected and injected into five Swiss mice. Four hours post-injection, the blood was collected and the parasites maturated in vitro for 18 to 26 hours. The parasites were counted according to their nuclei number using Giemsa stained blood smears.

DESCRIPTION OF THE PREFERRED EMBODIMENTS

Figure 1A:
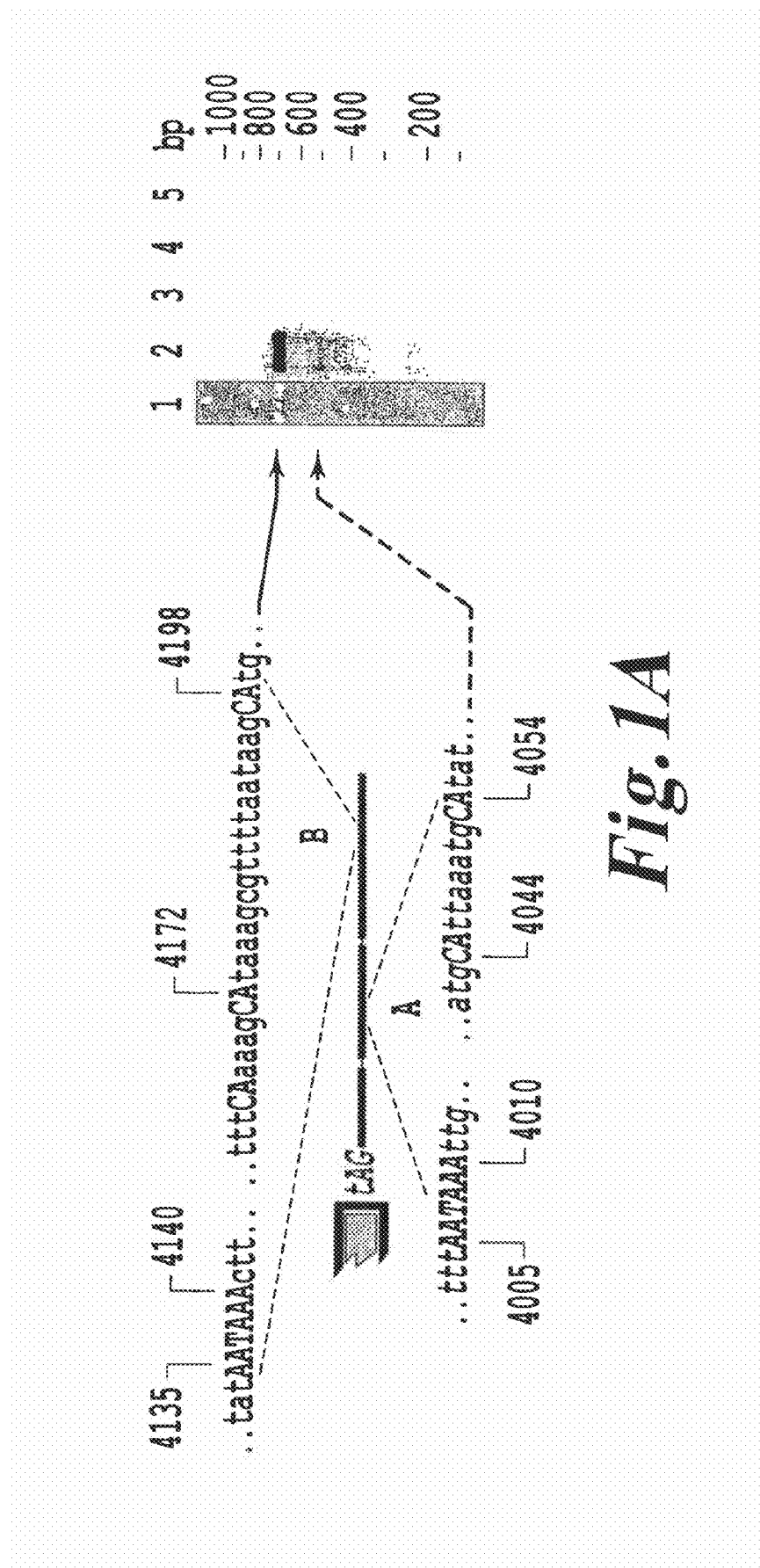

The 3'UTR of Pbsub2 was first characterised based on 3'RACE experiments using total RNA preparations from mature *P. berghei* schizonts (FIG. 1A). A major 750 bp and a weak 550 bp fragments hybridising to the Pbsub2 C-ter probe were amplified, consistent with the two predicted canonical polyadenylation motifs (AAUAAA) (SEQ ID NO: 1) (FIG. 1A, diagram). The sequence of six clones corresponding to the major 750 bp fragment revealed three different mRNA species with poly-A addition following CA dinucleotides 37, 43 and 62 bp respectively downstream from the distal and principally used AAUAAA (SEQ ID NO: 1) polyadenylation motif (FIG. 1A; Supplemental FIG. 2).

Figure 1B:
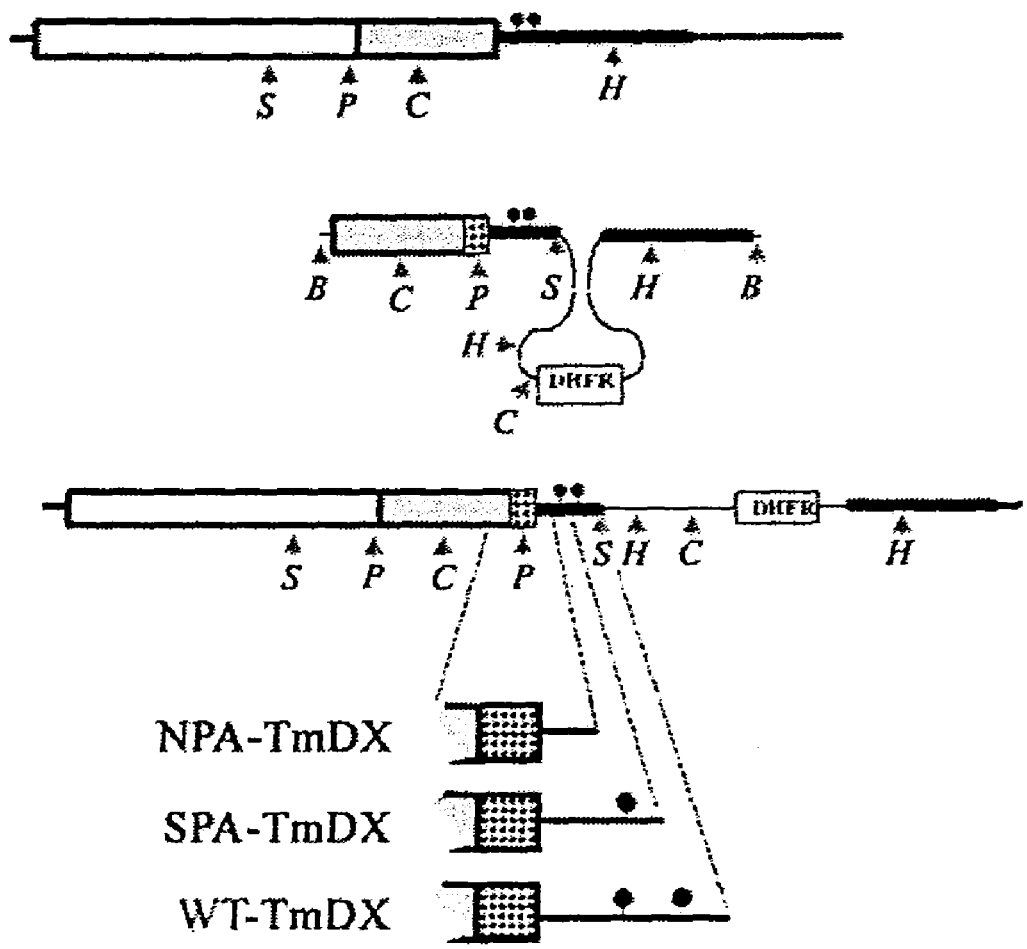
Figure 1C:
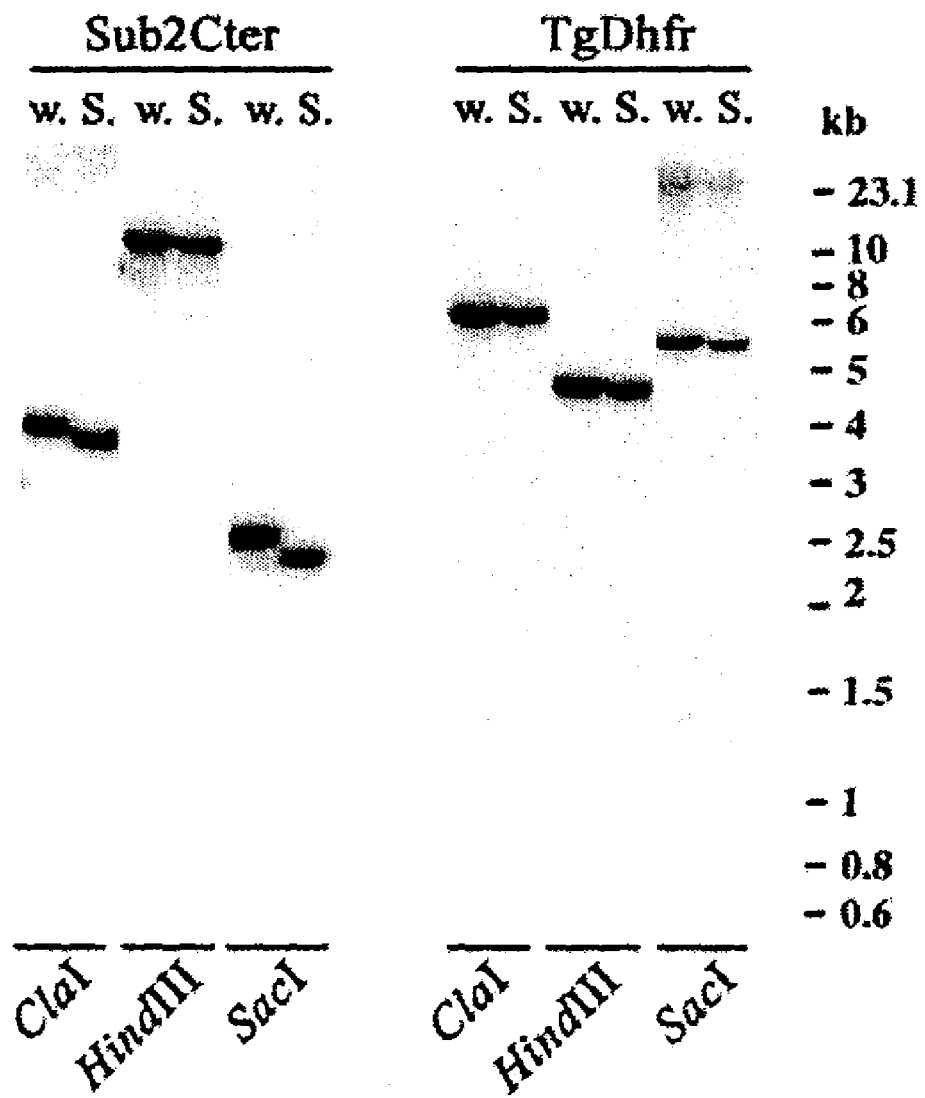

Two constructs were designed to sequentially delete Pbsub2 polyadenylation sites (FIG. 1B) following a double crossing-over event, giving rise respectively to the WT-TmDX[6], SPA-TmDX (Single PolyAdenylation site, corresponding to the proximal Pbsub2 polyadenylation site) and the NPA-TmDX (no polyadenylation site) recombinant parasites (FIG. 1B). Despite several attempts, the NPA-TmDX recombinant parasites were not recovered, while SPA-TmDX and WT-TmDX recombinant parasites were reproducibly selected using the same pool of parasites prepared for transfection experiments. The structure of the Pbsub2-locus from in vivo cloned recombinant parasites was assessed by Southern and chromosomal blots (FIG. 1C; Supplemental FIG. 1) and by PCR analyses.

The merozoite PbSUB2 protease being essential for the erythrocytic cycle, since the inability to delete both Pbsub2 polyadenylation sites shows that the Pbsub2 transcript polyadenylation following canonical AAUAAA (SEQ ID NO: 1) sites is crucial for the correct expression of the PbSUB2 protease.

Plasmid pSPA from which *Plasmodium* SPA-TmDX can be obtained, has been deposited at the CNCM on May 3, 2005 under accession number I-3423.

Interestingly, the 3'UTRs of *P. yoelii* and *P. falciparum* sub2 orthologs display similar polyA-addition motifs, (Supplemental FIG. 2), suggesting a trans-species conserved post-transcriptional modification for the sub2 transcripts.

In eukaryotic cells, the use of canonical AAUAAA (SEQ ID NO: 1) and CA motifs to trigger polyadenylation involves a set of conserved proteins which form a complex after binding to the poly-addition motifs[15]. Data mining of the *P. yoelii* and *P. falciparum* genomes identifies putative orthologs of these proteins: a Poly-A Polymerase III (PAP), a Cleavage and Polyadenylation Stimulation Factor (CPSF), a Cleavage and Stimulation Factor (Cstf) and a Cleavage Factor I (CF1) that are respectively >33%, 50%, >30% and 30% identical to their eukaryotic counterparts (Supplemental Table 1). While *P. falciparum* putative PAP mRNA expression is constitutive, the CPSF-like, Cstf-like and SUB2 mRNAs are concomitantly expressed during the merozoite biogenesis[5,6,9,10]. Therefore, although poly-A addition has previously been shown to occur at unusual sites[14,18], malaria parasites possess a classical stage regulated eukaryotic polyadenylation machinery which could be involved in post-transcriptional regulation of mRNA expression.

As suggested by the data in Supplemental Table 1, the regulation of mRNA transcription or post-translational regulation of mRNA stability, as observed for the sub2 gene may also represent virulence factors for other *Plasmodium* proteins. Thus, alteration of mRNA transcription efficiency or mRNA stability for transcripts of these genes could affect virulence of *Plasmodium*. Many other bloodstream and intracellular parasites also encode enzymes involved in the maturation of antigens involved in attachment or invasion of host cells. Thus, a similar regulation of mRNA transcription or mRNA stability via sites in the 3'UTR of maturation enzymes in organisms such as *Trypanosomes, Leishmania, Babesia* and *Toxoplasma* may represent important virulence factors in these organisms as well. Therefore, the methods employing the *Plasmodium* sub2 gene, sub2 gene mRNA transcript, and SUB2 protein may also be applied to the genes and gene products from parasites other than *Plasmodium* in an analogous manner.

Figure 2A:
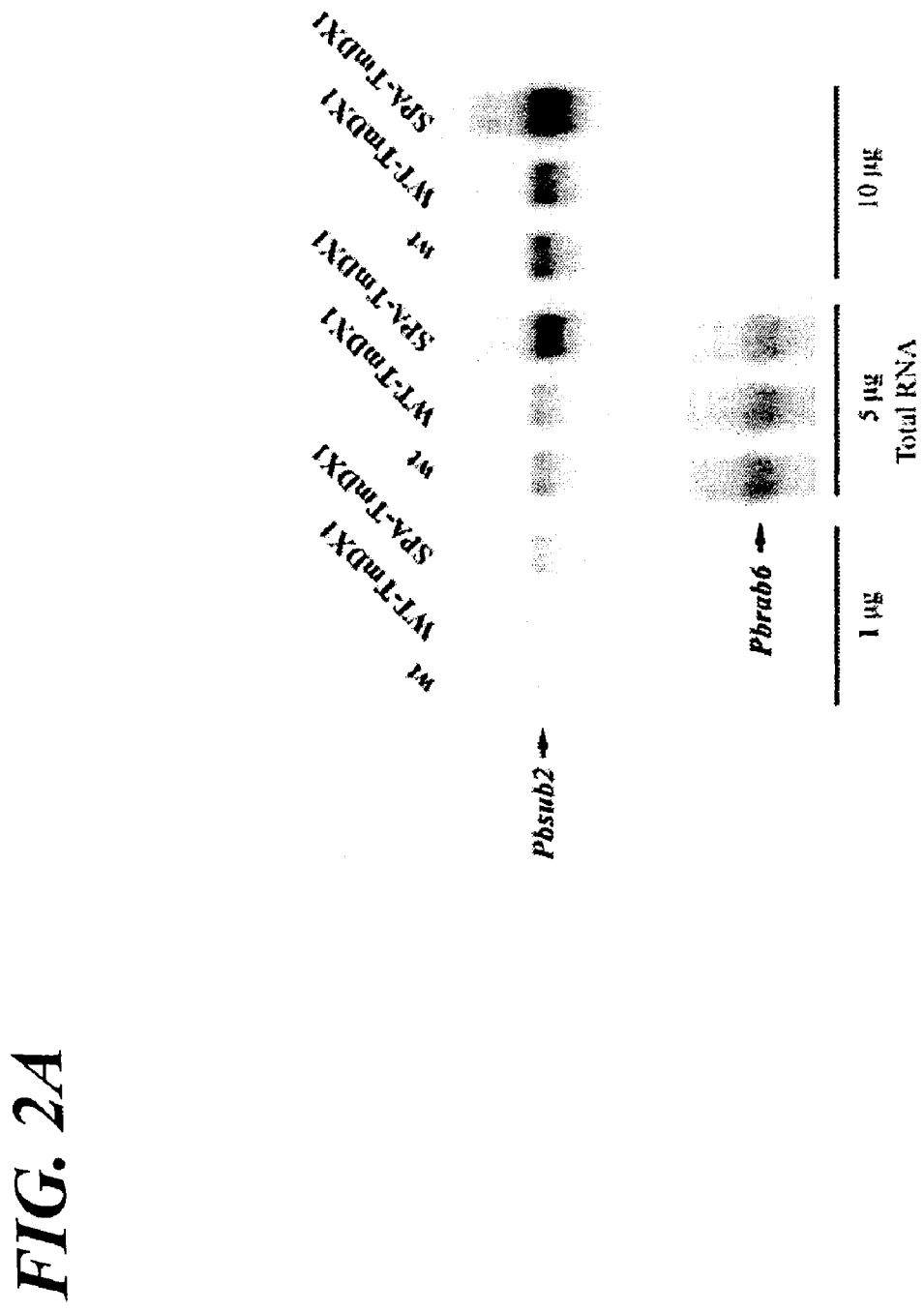
Figure 2B:
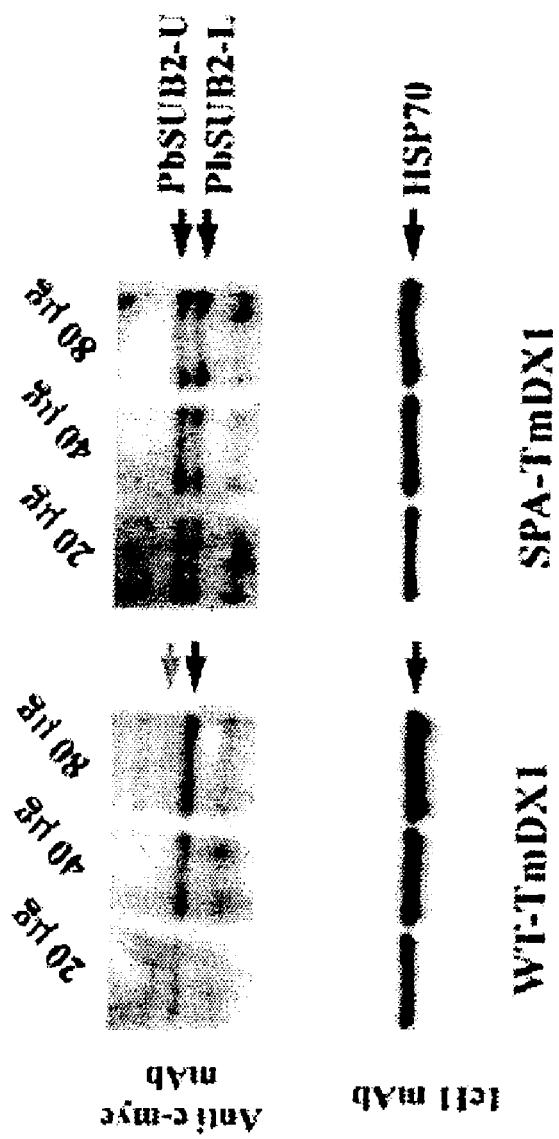
Figure 2C:
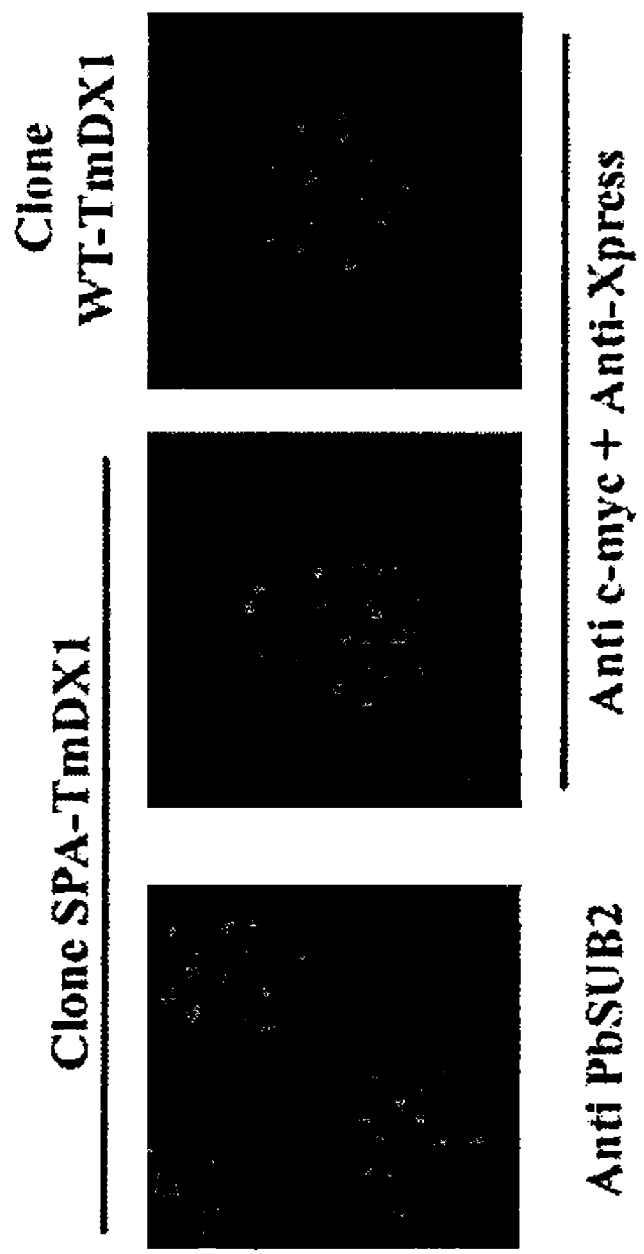

Quantitative Northern blot experiments revealed a 3 to 4 fold increase of the Pbsub2-mRNA in the SPA-TmDX1 clone compared to wild-type and WT-TmDX1 parasites (FIG. 2A and Supplemental Table 2). Whether this phenotype is a consequence of a modified Pbsub2-mRNA transcription efficiency or stability is unknown, but it correlates with a two-fold increase of the recombinant SPA-TmDX1 PbSUB2-protein (FIG. 2B and Supplemental Table 3). PbSUB2 protein principally accumulates as its intermediate activation form, whose final maturation takes place during its post-reticulum secretion[21]. Thus, the post-translational processing and localisation (FIG. 2C) of the SPA-TmDX1 PbSUB2-protein are identical to that found in wild-type parasites, indicating that the excess of PbSUB2 is available for further activation to perform its biological role.

To investigate the potential effects of PbSUB2 over-expression during the intra-erythrocytic parasite development, the inventors first compared the kinetics of schizogony by measuring the ratio of the 2-4, 4-8, and >8 nuclei during a comparative in vitro maturation of highly synchronised WT-TmDX1 and SPA-TmDX1 parasites (Supplemental FIG. 3). Their timing of nuclei multiplication, average number of merozoites per schizont and erythrocytic cycle duration were not significantly different. This result is in accordance with the fact that PbSUB2 is a merozoite-specific enzyme which is not detectable in other parasite blood stages[5,6]. A contrario, when analysing in detail mature SPA-TmDX1 merozoites, it appears that the accumulation of PbSUB2 results in a significant increase of respectively the merozoite surface PbAMA1 15 kDa-C-terminal ((PbAMA1-CT15) and PbMSP1-19 maturation products (FIG. 3 & Supplemental Tables 4 and 5).

Figure 4A:
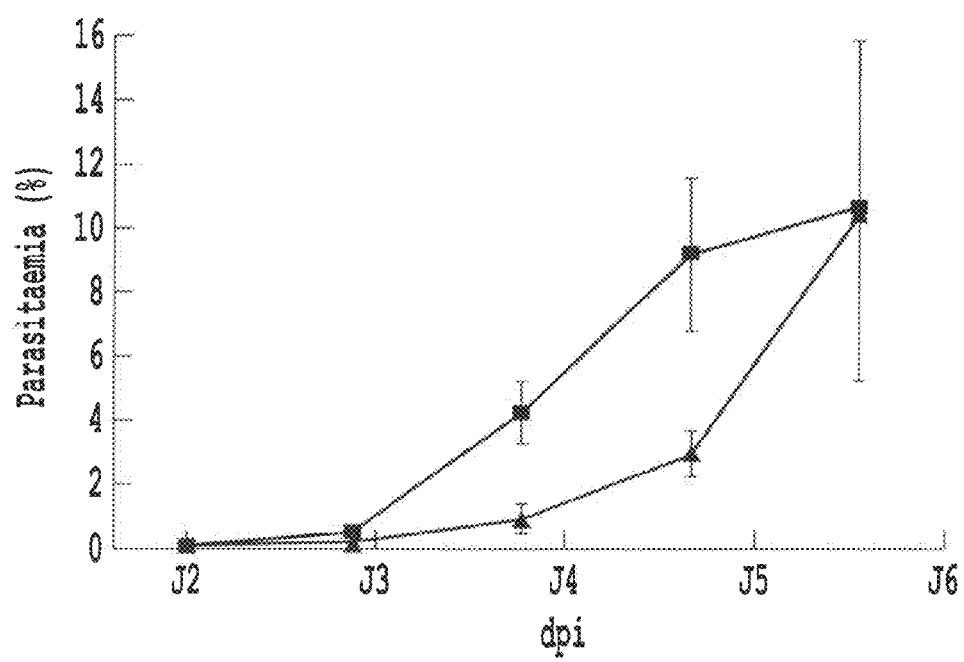
Figure 4B:
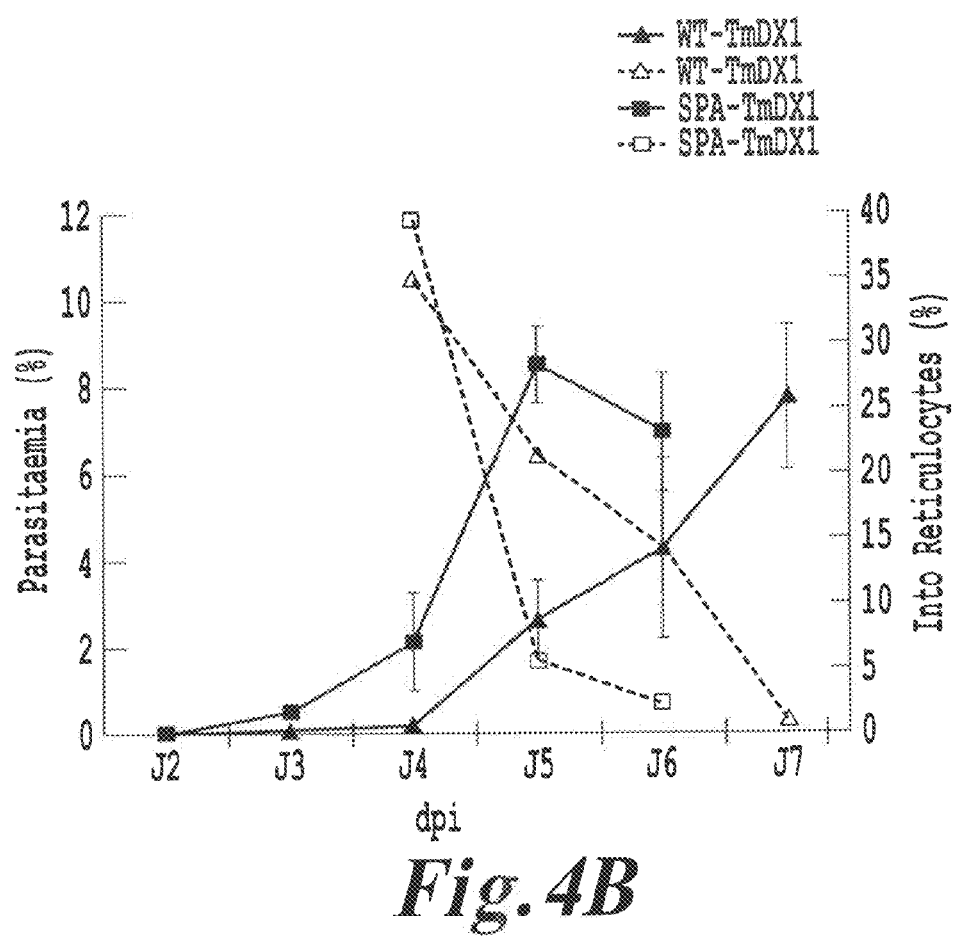
Figure 5A:
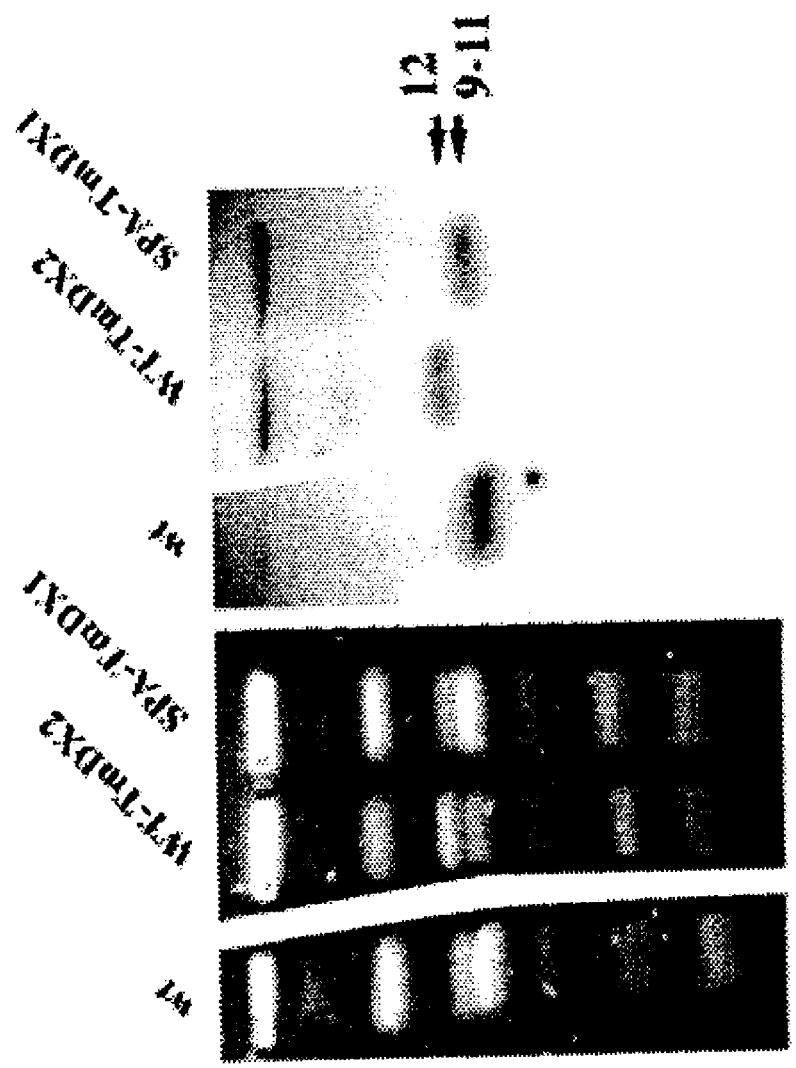
Figure 5B:
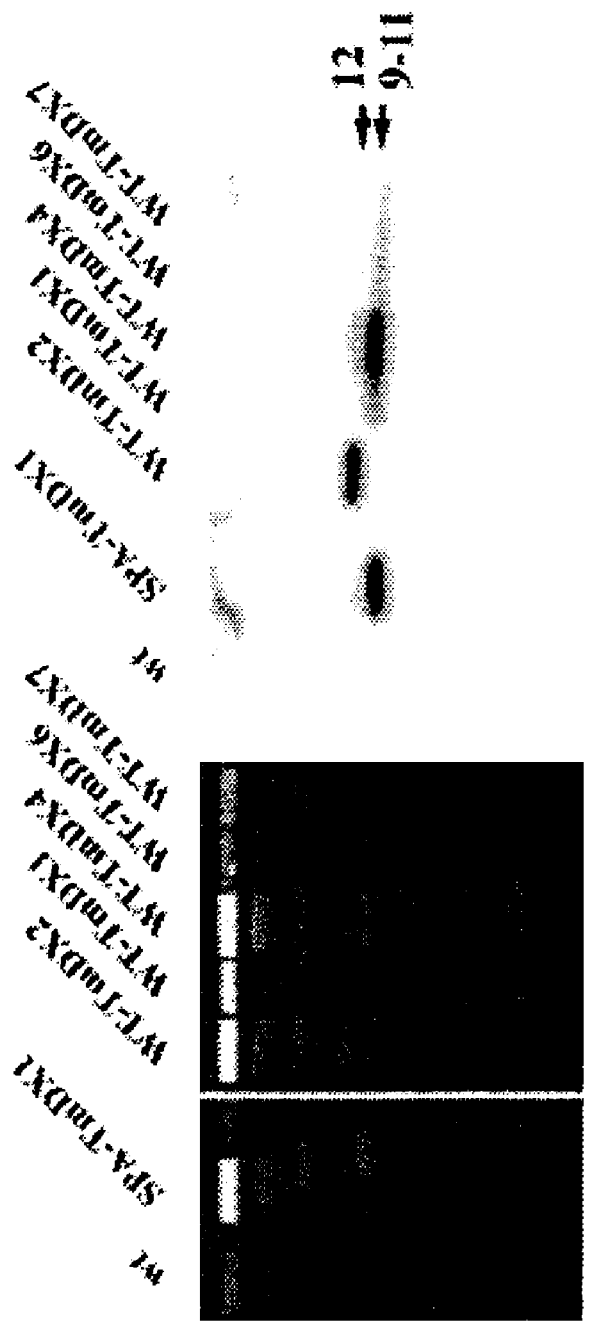

The maturation of the merozoite surface MSP1-42 and the AMA1 has been shown to play a crucial role during the invasion process per se. The inventors have now determined that this observation which was obtained in vitro correlates with a virulence phenotype in vivo. As shown by the FIG. 4, SPA-TmDX1 parasites grow statistically faster in vivo than WT-TmDX1. This behaviour is independent from the host genetic background, since the injection of $5.10^4$ parasites to Swiss (not shown), C57B1/6J and BALB/cJ yields to respectively 84% and 46% increase of the multiplication rates in vivo for the PbSUB2 over-expressing SPA-TmDX1 parasites (FIG. 4 and Methods). The SPA-TmDX1 parasites increased growth rate in vivo leads to the death of the infected mice one day before the WT-TmDX1 infected ones. Thus, the 3'UTR-driven accumulation of PbSUB2 protein in SPA-TmDX1 parasites results in a significant increase of the parasite virulence in vivo.

The WT-TmDX1 and SPA-TmDX1 clones derive from *P. berghei* ANKA parasites, harbouring a marked tropism for reticulocytes[22]. Thus, the inventors investigated whether the multiplication rate difference between these clones was related to a better invasion of normocytes by SPA-TmDX1 parasites. At day 4 (2.5% parasitaemia), more than 30% of both WT-TmDX1 and SPA-TmDX1 parasites were detected in reticulocytes (FIG. 3B); when SPA-TmDX1 and WT-TmDX1 parasitaemia reached 8.5% and 7.8% on day 5 and 7 respectively, the proportion of parasites in reticulocytes decreased to 2.7% and 1.1% respectively. Based on these observations, PbSUB2 accumulation does not impair *P. berghei* tropism in vivo. The 2 day quicker consummation of reticulocytes being a consequence of the SPA-TmDX1 clone's higher multiplication rate in toto.

As a more general concern, the increase of *P. berghei* virulence in vivo following the modification of the Pbsub2 3'UTR indicates that malaria parasite virulence can be potentiated following the mutation of a single gene regulatory element. Preliminary results indicate that the *P. falciparum* Pfsub2 3'UTR is highly polymorphic and could lead to *Plasmodium falciparum* parasites over-expressing PfSUB2. Adaptation of parasite gene expression to a selective pressure has been shown to participate in the resistance to anti-malarials[20,25]. Thus, non-coding regions involved in the regulation of expression of crucial *Plasmodium* genes should now be considered as potential virulence factors, a situation already reported for some viruses and bacteria[26-28].

This large latent reservoir of virulence may not yet have been explored by the parasite but could be revealed under a sub-lethal selective pressure, such as a partial immunity driven by vaccines which reduces pathogen growth rate[29,30]. Since the selection of such vaccine overcoming parasites is not anticipated in clinical trials, and considering the large population targeted, this observation may lead to dramatic consequences for public health following imperfect intervention strategies against malaria parasites, or other invasive pathogens.

Malaria pathogens include those which infect humans, simians and other animals, for example, *Plasmodium berghei, Plasmodium brasilianum, Plasmodium chabaudi, Plasmodium cynomolgi, Plasmodium falciparum, Plasmodium gallinaceum, Plasmodium knowlesi, Plasmodium lophurae, Plasmodium malariae, Plasmodium ovale, Plasmodium reichenowi* and *Plasmodium vivax*.

The following sequences are incorporated by reference. *P. falciparum* SUB2 (AJ132006 and NC_004315, geneID: 810927); *P. yoelii* SUB2 (PY01222, proteinID: EAA20512.1); *Toxoplasma gondii* SUB2 and SUB1 (AF420596 and AY043483, respectively). Detailed information about the structures and functions of 3'UTR is incorporated by reference to Proudfoot et al., Curr. Biol. 12:R855-7 (2002).

A recombinant *Plasmodium* according to the invention may comprise a modified regulatory segment within the 3'UTR. Such a modification may increase or decrease the expression of a gene like sub2, which encodes a protein involved in maturation or post-translational processing of other parasite antigens, such as the SER2 subtilisin-like maturase. Recombinant organisms having modifications in the 3'UTR which provide higher amounts of a maturase like SUB2 have been demonstrated to be more virulent compared to the corresponding unmodified strains. Similarly, recombinant strains modified to express less of a maturase like SUB2 (e.g., an attenuated strain) would be expected to be less virulent. An example of a use for a less virulent strain would be as a live vaccine or as a comparative control. More virulent strains can be used in vaccine testing procedures, for example, to test the efficacy of a particular vaccine, to provoke particular humoral or cellular immune responses, or as comparative controls in assays involving *Plasmodium* strains with other virulence characteristics.

To detect or evaluate the virulence of a *Plasmodium* strain, the amount of SUB2 protein expressed by that strain compared to a control strain may be determined Alternatively, the amount of sub2 mRNA may be detected or measured as a comparative indication of virulence of the test and control strains. Methods for determining the levels a particular protein, such as SUB2, are well known in the art, for example, SUB2 levels may be determined by ELISA or Western blotting using antiserum to SUB2 epitopes. The mRNA encoding SUB2 may also be determined or quantified by conventional methods.

Methods for determining the amount of mRNA (or corresponding cDNA) encoding a *Plasmodium* protein such as SUB2, AMA1 or MSP-1 are well known in the art and are also incorporated by reference to *Current Protocols In Molecular Biology*, Chapter 25 (2005) which is incorporated by reference.

Western blotting and other methods of identifying or quantitating the amounts of a particular protein, such as SUB2, AMA1 or MSP-1 are well known in the art and are also incorporated by reference to *Current Protocols in Molecular Biology*, e.g. Chapters 10 and 11 (2005) which is incorporated by reference.

For some applications, proteins that are essentially identical or at least 90%, 95%, or 99% similar to SUB2, AMA1 or MSP-1 may be used to construct a recombinant *Plasmodium* according to the present invention. Generally, a nucleic acid sequence encoding a variant will have 70%, preferably 80%, more preferably 90, 95 or 99% similarity to a native sequence. Such similarity may be determined by an algorithm, such as those described by *Current Protocols in Molecular Biology*, vol. 4, chapter 19 (1987-2005) or by using known software or computer programs such as the BestFit or Gap pairwise comparison programs (GCG Wisconsin Package, Genetics Computer Group, 575 Science Drive, Madison, Wis. 53711). Best-Fit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Likewise, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Coding sequences for these proteins may also be determined by the ability of a polynucleotide to hybridize under stringent conditions to the complement of a coding region of a known SUB2, AMA1 or MSP-1 gene. Such hybridization conditions may comprise hybridization at 5×SSC at a temperature of about 50 to 68° C. Washing may be performed using 2×SSC and optionally followed by washing using 0.5× SSC. For even higher stringency, the hybridization temperature may be raised to 68° C. or washing may be performed in a salt solution of 0.1×SSC. Other conventional hybridization procedures and conditions may also be used as described by *Current Protocols in Molecular Biology*, (1987-2005), see e.g. Chapter 2.

The polynucleotide of the invention which comprises a *Plasmodium* subtilisin-like maturase SUB2 untranslated region and a regulatory segment differs from the corresponding native sequence. The difference may be in the deletion or addition of a regulatory segment, such as a polyadenylation site, or in the polynucleotide sequence of a regulatory segment.

The deletion, addition or alteration of the regulatory segment provides a different degree of SUB2 protein expression (it modulates protein expression) than that of the corresponding native sequence. The polynucleotide may be conveniently isolated or purified from other nucleic acids or components of *Plasmodium*. The alteration in the regulatory sequence of the 3'UTR may occur within a polyadenylation site. Such a regulatory segment or polyadenylation site may conform to the native motif, but have 1, 2, 3, 4, 5 or more nucleotides deleted, inserted or substituted compared to the native sequence. Preferably, an altered regulatory segment will contain a high degree of similarity to the native sequence, e.g. 60, 70, 80, 90, 95% similarity, but will function to increase or decrease SUB2 expression compared to the native sequence. Such increases may range from 1, 2, 5, 10, 20, 50, 100, 200% or more compared to the level of expression of SUB2 provided by the unmodified native sequence. Similarly, a modified regulatory sequence may decrease SUB2 expression down to 95, 90, 80, 75% 50, 40, 25, 10, 5% or less of SUB2 expression provided by the unmodified native regulatory sequence. The same parameters apply to regulatory sequences for other non-SUB2 genes involved in antigen or polypeptide processing in *Plasmodium* or other parasites.

Figure 6:
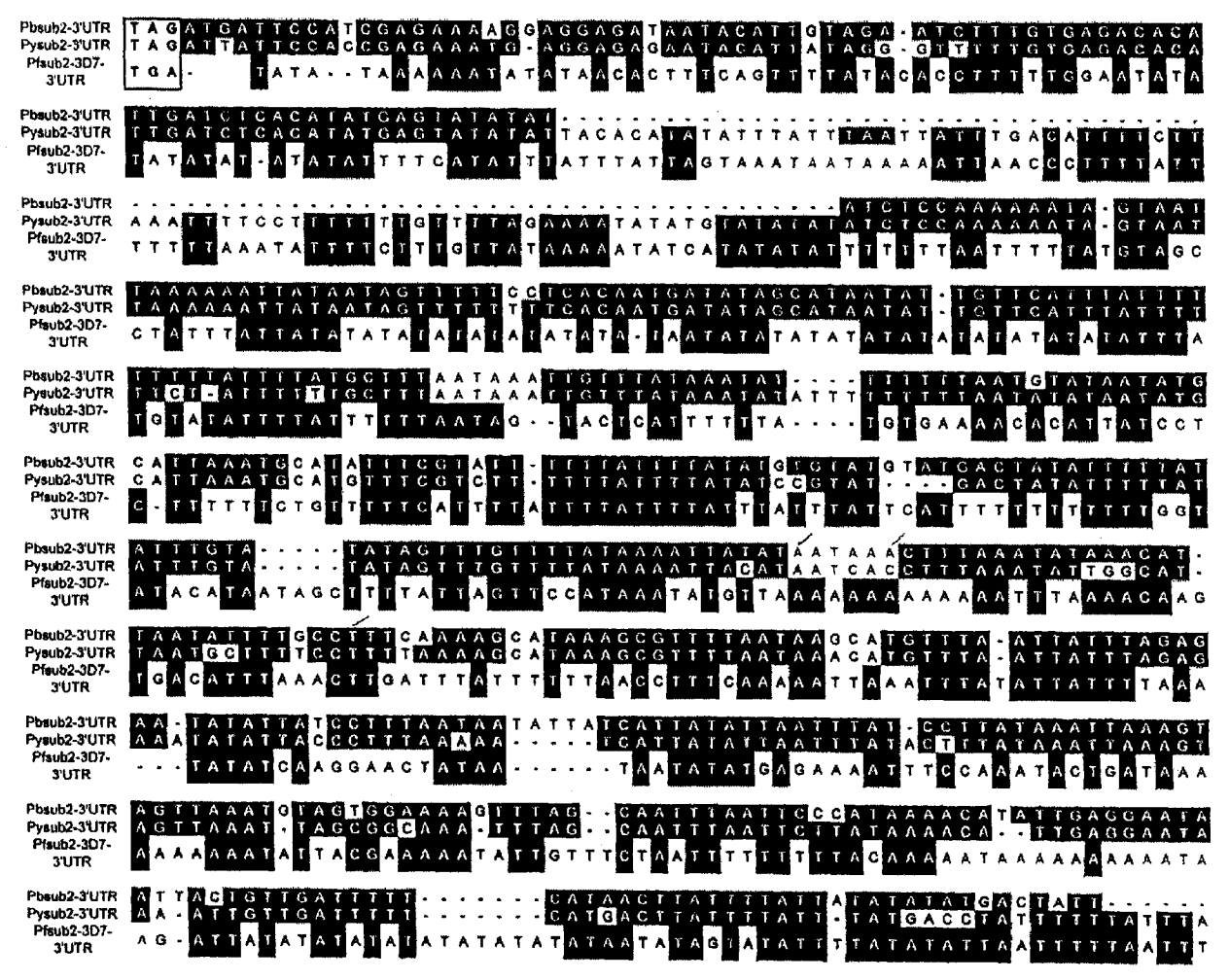

Polyadenylation sites or other motifs in a 3'UTR may be identified using software such as CLUSTALW. Sequences and/or motifs shared by the 3'UTRs of Plasmodium species are also graphically described by SEQ ID NOS: 2, 3, and 4 in FIG. 6.

High-throughput screening of candidate molecules is known in the art. U.S. Pat. No. 6,770,451 describes a method for screening enzyme inhibitors, U.S. Pat. No. 6,368,789 describes a method for identifying telomerase inhibitors and U.S. Pat. No. 6,051,373 describes methods for screening inhibitors of the transcription-enhancing activity of the X protein of hepatitis B virus. The screening methods and libraries disclosed by these patents is incorporated by reference. None of these documents disclose the use of the SUB2 target molecule of the present invention. Combinatorial Chemistry vol. 8, issue 1, pp. 1-5 by N. K. Terrett (January, 2006) also describes a number of different methods and libraries for high throughput screening of anti-malaria agents. These methods and libraries are also incorporated by reference. Large numbers of test compounds may be efficiently screened for their ability to bind and/or inhibit SUB2 activity. These test compounds may have various structures, such as small organic molecules having a molecular mass of about 50 to 2,500 daltons, molecules containing metal ions, carbohydrates, saccharides, peptides having less than 100 residues, polypeptides, antibodies, and molecules or other products isolated from natural sources such as from bacteria, fungi, parasites, plants, and animals.

EXAMPLES

Methods

Parasites. *P. berghei* parasites were amplified and collected as previously described[6]. Noteworthily, due to the reactivity of the anti-c-myc-specific monoclonal antibody (mAb) with the host 30 kDa Myc proteins, special care was taken to deplete leucocytes using Plasmodipur filters (Euro-Diagnostica, the Netherlands), before preparing erythrocyte extracts for Western blotting experiments.

Polyadenylation sites mapping. RT-PCR analyses were performed with 1 µg of total RNA as previously described[6]. The 3' untranslated region of Pbsub2 was reverse transcribed from 1 µg of total segmented-schizont RNA using the Tun primer (5'TTTTTTTTTTTTTTTTTTTT[ACG][ACGT]3') (SEQ ID NO: 5). The resulting cDNA was PCR amplified using the Tun and CterBamHI (5'TTTGGATCCCATCAT-CAAAGTAAACAACGCG3') (SEQ ID NO: 6) primers (95° C., 20 sec; 45° C., 1 min, 62° C., 2 min for 3 cycles; then 95° C., 20 sec; 50° C., 1 min; 62° C., 2 min for 30 cycles), separated in 1% agarose gels, cloned into the pCR2.1-TOPO vector (Invitrogen), and sequenced using a Sequenase 2 kit (USB corporation).

Generation of transfected constructs. The pSub2-SPA-TmDX and pSub2-NPA-TmDX plasmids were obtained following the same three step procedure used for the pSub2-WT-PA plasmid, with the following modifications[6]. The Pbsub2-3'UTR fragments used to generate the pSub2-SPA-TmDX and pSub2-NPA-TmDX plasmids were PCR amplified with the reverse primers 5'CCGGATCCATAAAAATATAGT-CATACATAC3' (SEQ ID NO: 7) and 5'CCGGATCCATAT-TATGCTATATCATTGTGA3' (SEQ ID NO: 8) respectively. The constructs were entirely sequenced prior to transfection.

Parasite transfection and nucleic acids analyses. Seventy micrograms of each BsmI digested plasmid DNA were transfected into purified schizonts of the *P. berghei* ANKA strain and pyrimethamine selection of the transformed parasites were performed as previously described[6]. The pSub2-SPA-TmDX transfected parasites were cloned by limiting dilution as previously described[6]. Southern and Northern blot analyses were performed as described with the appropriate probe[6]. The Rab6 probe was PCR amplified using the 5'TTGG-GAGAACAAGCAGTTGG3' (SEQ ID NO: 9) and 5'GTAAC-CTTTCTAAGATCGGCC3' (SEQ ID NO: 10) primers, and dATP[$\alpha^{32}$P] labelled (Megaprime, AP Biotech). The Northern blot bands were quantified using the Quantity One software (Biorad).

Seventy micrograms of each BsmI digested plasmid DNA were transfected into purified schizonts of the *P. berghei* ANKA strain and pyrimethamine selection of the transformed parasites were performed as previously described[6]. The pSub2-SPA-TmDX transfected parasites were cloned by limiting dilution as previously described[6]. Southern and Northern blot analyses were performed as described with the appropriate probe[6]. The Rab6 probe was PCR amplified using the 5'TTGGGAGAACAAGCAGT-TGG3' (SEQ ID NO: 9) and 5'GTAACCTTTCTAAGATCG-GCC3' (SEQ ID NO: 10) primers, and dATP[$\alpha$32P] labelled (Megaprime, AP Biotech). The Northern blot bands were quantified using the QUANTITY ONE@ software (Biorad).

Immunodetection. For PbSUB2 quantification, total proteins were extracted from WT-TmDX1 and SPA-TmDX1 parasites using 2% SDS and quantified following the Folin method (Sigma) prior to gel loading. Western blot analyses were performed as described[6] using 1:5000 diluted horseradish peroxidase (HRP) coupled c-myc mAb or 1:5000 diluted 1c11 mAb, revealed with HRP coupled secondary antibodies. The 1c11 and c-myc mAb labelling was detected using Super-Signal Pico and SuperSignal Femto reagents respectively (Pierce). The bands were quantified using the QUANTITY ONE® software (Biorad).

Immunofluorescence assays were performed on air-dried thin films of *P. berghei* infected erythrocytes using 1:50 diluted Sub2Cter-GST sera or 1:100 diluted anti-c-myc and anti-Xpress mAb as previously described[6]. Primary antibodies were revealed using ALEXAFLUOR GREEN® anti-mouse antibodies (Molecular Probes).

In vivo infection of mice and determination of the average daily multiplication rate.

The average daily multiplication rate (ADMR) was calculated as:

$$ADMR=\{[Parasitaemia \times (1 \times 10^{10})]/(5 \times 10^4)\}^{1/4}$$

where $1 \times 10^{10}$ and $5 \times 10^4$ stand respectively for the erythrocyte total number per mouse and the total number of parasites injected at day 0. The ADMR values obtained are 9.5 and 8.1 for SPA-TmDX1 and 6.5 and 4.4 for WT-TmDX1 parasites in BALB/cJ and C57B1/6J mice respectively.

SUPPLEMENTAL TABLE 1

Description of the putative parasite orthologs involved in the polyadenylation addition. Data were extracted from www._plasmodb.org, Bahl et al., (2003).

| Abbreviation | Name | PlasmoDB access number | Chomosome location | Minimum % of identity with eukaryotic putative orthologues |
|---|---|---|---|---|
| CPSF | Cleavage and Polyadenylation Stimulation factor | PFC0825w PY00757 | PFC0825w: 3 | 50% of identity with eukaryotic putative orthologues |
| Cstf | Cleavage Stimulation factor | PFI1600w PY02603 | PFI1600w: 9 | 30% of identity with eukaryotic putative orthologues |
| PAP | PolyA Polymerase III | PFF1240w PY02044 | PFF1240w: 6 | 33-40% of identity with eukaryotic putative orthologues |
| CF1 | Cleavage Factor I | PFA0450c | PFA0450c: 1 | 30% of identity with *A. thaliana* CF1 |

PlasmoDB: the *Plasmodium* genome resource.
A database integrating experimental and computational data. Nucleic acids research, 31, 212-215).

SUPPLEMENTAL TABLE 2

Quantification of the Pbsub2 mRNA in wild-type, WT-TmDX1 and SPA-TmDX1 parasites.

| | Wild Type | | | WT-TmDX1 | | | SPA-TmDX1 | | |
|---|---|---|---|---|---|---|---|---|---|
| | 1 µg | 5 µg | 10 µg | 1 µg | 5 µg | 10 µg | 1 µg | 5 µg | 10 µg |
| Pbsub2 mRNA | nd | 138 | 347 | nd | 128 | 373 | 47 | 541 | 1011 |
| $\frac{SPA\text{-}TmDX1\ value}{x}$ Ratio | | 3.9 | 2.9 | | 4.2 | 2.7 | | | |

The amounts of mRNA are presented in arbitrary units.
The ratios of SPA-TmDX1 over wild type and WT-TmDX1 intensity counts are presented
nd: not determined.

SUPPLEMENTAL TABLE 3

Quantification of the PbSUB2 protein from WT-TmDX1 and SPA-TmDX1 extracts.

|  | WT-TmDX1 | | | SPA-TmDX1 | | |
| --- | --- | --- | --- | --- | --- | --- |
|  | 20 μg | 40 μg | 80 μg | 20 pg | 40 μg | 80 μg |
| PbSUB2 | 115 | 253 | 516 | 238 | 457 | 627 |
| HSP70 | 2623 | 3372 | 3935 | 2315 | 2863 | 3372 |
| $\frac{PbSUB2}{HSP70}$ Ratio (1) | 0.044 | 0.075 | 0.131 | 0.103 | 0.160 | 0.186 |
| $\frac{WT\text{-}TmDX1\ Ratio\ (1)}{SPA\text{-}TmDX1\ Ratio\ (1)}$ Ratio (2) |  |  |  | 2.3 | 2.1 | 1.4 |

The amounts of PbSUB2 and PbHSP70 proteins are presented in arbitrary units.
The ratio between PbSUB2 and HSP70 corresponding to the corrected amount of PbSUB2 is presented (1).
The ratio between PbSUB2 corrected amounts from WT-TmDX1 and SPA-TmDX1 protein extracts are presented in bold (2).

SUPPLEMENTAL TABLE 4

Quantification of the AMA1 protein from WT-TmDX1 and SPA-TmDX1 extracts.

|  | WT-TmDX1 | | SPA-TmDX1 | |
| --- | --- | --- | --- | --- |
| Parasites | $6.5 \times 10^7$ | $13 \times 10^7$ | $6.5 \times 10^7$ | $13 \times 10^7$ |
| PbAMA1-CT15 | 104 | 606 | 1140 | Out of range |
| HSP70 | 668 | 1017 | 751 | 1603 |
| $\frac{PbAMA1\text{-}CT15}{HSP70}$ Ratio (1) | 0.16 | 0.60 | 1.52 | / |
| $\frac{SPA\text{-}TmDX1\ Ratio\ (1)}{WT\text{-}TmDX1\ Ratio\ (1)}$ Ratio (2) |  |  | 9.7 | / |

The amounts of PbAMA1-CT15 and PbHSP70 proteins are presented in arbitrary units.
The ratio between PbAMA1-CT15 and PbHSP70 corresponding to the corrected amount of PbAMA1 is presented (1).
The ratio between PbAMA1-CT15 corrected amounts from WT-TmDX1 and SPA-TmDX1 protein extracts is presented in bold (2).

SUPPLEMENTAL TABLE 5

Quantification of the PbMSP1-19 protein from WT-TmDX1 and SPA-TmDX1 extracts.

|  | SPA-TmDX1 | | | WT-TmDX1 | | |
| --- | --- | --- | --- | --- | --- | --- |
| Parasites | $13 \times 10^6$ | $6.5 \times 10^6$ | $1.3 \times 10^6$ | $13 \times 10^6$ | $6.5 \times 10^6$ | $1.3 \times 10^6$ |
| PbMSP1-19 | 7380 | 5189 | 1599 | 3725 | 1911 | 464 |
| HSP70 | 2541 | 2079 | 796 | 2636 | 1892 | 664 |
| $\frac{PbMSP1\text{-}19}{HSP70}$ Ratio (1) | 2.90 | 2.50 | 2.01 | 1.41 | 1.01 | 0.70 |
| $\frac{SPA\text{-}TmDX1\ Ratio\ (1)}{WT\text{-}TmDX1\ Ratio\ (1)}$ Ratio (2) | <u>2.1</u> | <u>2.5</u> | 2.9 |  |  |  |

The amounts of PbMSP1-19 and PbHSP70 proteins are presented in arbitrary units.
The ratio between PbMSP1-19 and PbHSP70 corresponding to the corrected amount of PbMSP1-19 is presented (1).
The ratio between PbMSP1-19 corrected amounts from WT-TmDX1 and SPA-TmDX1 protein extracts are presented in bold (2).
Underlined values correspond to under-estimated ratios due to the saturation of the signal on the film.

Modifications and Other Embodiments

Various modifications and variations of the described products and methods and their methods of use as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Modifications of the described modes of the invention which would be obvious to those skilled in the microbiological, parasitological, molecular biological, diagnostic, therapeutic, pharmacological and biochemical arts or related fields are intended to be within the scope of the following claims.

CITATIONS

1. Mackinnon, M. J. & Read, A. F. Virulence in malaria: an evolutionary viewpoint. *Philos Trans R Soc. Lond B Biol Sci* 359, 965-86 (2004).
2. Breman, J. G., Alilio, M. S. & Mills, A. Conquering the intolerable burden of malaria: what's new, what's needed: a summary. *Am J Trop Med Hyg* 71, 1-15 (2004).
3. Chotivanich, K. et al. Parasite multiplication potential and the severity of *falciparum* malaria. *J Infect Dis* 181, 1206-9 (2000).
4. Rasti, N., Wahlgren, M. & Chen, Q. Molecular aspects of malaria pathogenesis. *FEMS Immunol Med Microbiol* 41, 9-26 (2004).
5. Barale, J. C. et al. *Plasmodium falciparum* subtilisin-like protease 2, a merozoite candidate for the merozoite surface protein 1-42 maturase. *Proc Natl Acad Sci USA* 96, 6445-50 (1999).
6. Uzureau, P., Barale, J. C., Janse, C. J., Waters, A. P. & Breton, C. B. Gene targeting demonstrates that the *Plasmodium berghei* subtilisin PbSUB2 is essential for red cell 7. de Koning-Ward, T. F., Janse, C. J. & Waters, A. P. The development of genetic tools for dissecting the biology of malaria parasites. *Annu Rev Microbiol* 54, 157-85 (2000).
8. Gardner, M. J. et al. Genome sequence of the human malaria parasite *Plasmodium falciparum*. *Nature* 419, 498-511 (2002).
9. Bozdech, Z. et al. The transcriptome of the intraerythrocytic developmental cycle of *Plasmodium falciparum*. *PLoS Biol* 1, E5 (2003).
10. Le Roch, K. G. et al. Global analysis of transcript and protein levels across the *Plasmodium falciparum* life cycle. *Genome Res* 14, 2308-18 (2004).
11. Horrocks, P., Dechering, K. & Lanzer, M. Control of gene expression in *Plasmodium falciparum*. *Mol Biochem Parasitol* 95, 171-81 (1998).
12. Militello, K. T., Dodge, M., Bethke, L. & Wirth, D. F. Identification of regulatory elements in the *Plasmodium falciparum* genome. *Mol Biochem Parasitol* 134, 75-88 (2004).
13. Corredor, V. et al. A SICAvar switching event in *Plasmodium knowlesi* is associated with the DNA rearrangement of conserved 3' non-coding sequences. *Mol Biochem Parasitol* 138, 37-49 (2004).
14. Golightly, L. M., Mbacham, W., Daily, J. & Wirth, D. F. 3'UTR elements enhance expression of Pgs28, an ookinete protein of *Plasmodium gallinaceum*. *Mol Biochem Parasitol* 105, 61-70 (2000).
15. Proudfoot, N. & O'Sullivan, J. Polyadenylation: a tail of two complexes. *Curr Biol* 12, R855-7 (2002).
16. Jasiecki, J. & Wegrzyn, G. Growth-rate dependent RNA polyadenylation in *Escherichia coli*. *EMBO Rep* 4, 172-7 (2003).
17. Levitt, A., Dimayuga, F. O. & Ruvolo, V. R. Analysis of malarial transcripts using cDNA-directed polymerase chain reaction. *J Parasitol* 79, 653-62 (1993).
18. Ruvolo, V., Altszuler, R. & Levitt, A. The transcript encoding the circumsporozoite antigen of *Plasmodium berghei* utilizes heterogeneous polyadenylation sites. *Mol Biochem Parasitol* 57, 137-50 (1993).
19. Thathy, V. et al. Levels of circumsporozoite protein in the *Plasmodium* oocyst determine sporozoite morphology. *Embo J* 21, 1586-96 (2002).
20. Waller, K. L. et al. Chloroquine resistance modulated in vitro by expression levels of the *Plasmodium falciparum* chloroquine resistance transporter. *J Biol Chem* 278, 33593-601 (2003).
21. Blackman, M. J. Proteases in host cell invasion by the malaria parasite. *Cell Microbiol* 6, 893-903 (2004).
22. Deharo, E., Coquelin, F., Chabaud, A. G. & Landau, I. The erythrocytic schizogony of two synchronized strains of *Plasmodium berghei*, NK65 and ANKA, in normocytes and reticulocytes. *Parasitol Res* 82, 178-82 (1996).
23. Simpson, J. A., Silamut, K., Chotivanich, K., Pukrittayakamee, S. & White, N. J. Red cell selectivity in malaria: a study of multiple-infected erythrocytes. *Trans R Soc Trop Med Hyg* 93, 165-8 (1999).
24. Dutta, S., Haynes, J. D., Moch, J. K., Barbosa, A. & Lanar, D. E. Invasion-inhibitory antibodies inhibit proteolytic processing of apical membrane antigen 1 of *Plasmodium falciparum* merozoites. *Proc Natl Acad Sci USA* 100, 12295-300 (2003).
25. Myrick, A., Munasinghe, A., Patankar, S. & Wirth, D. F. Mapping of the *Plasmodium falciparum* multidrug resistance gene 5'-upstream region, and evidence of induction of transcript levels by antimalarial drugs in chloroquine sensitive parasites. *Mol Microbiol* 49, 671-83 (2003).
26. Edgil, D., Diamond, M. S., Holden, K. L., Paranjape, S. M. & Harris, E. Translation efficiency determines differences in cellular infection among dengue virus type 2 strains. *Virology* 317, 275-90 (2003).
27. Mangold, M. et al. Synthesis of group A streptococcal virulence factors is controlled by a regulatory RNA molecule. *Mol Microbiol* 53, 1515-27 (2004).
28. Stoecklin, G., Gross, B., Ming, X. F. & Moroni, C. A novel mechanism of tumor suppression by destabilizing AU-rich growth factor mRNA. *Oncogene* 22, 3554-61 (2003).
29. Gandon, S., Mackinnon, M. J., Nee, S. & Read, A. F. Imperfect vaccines and the evolution of pathogen virulence. *Nature* 414, 751-6 (2001).
30. Mackinnon, M. J. & Read, A. F. Immunity promotes virulence evolution in a malaria model. *PLoS Biol* 2, E230 (2004).

The invention claimed is:

1. An isolated or purified polynucleotide that is at least 95% identical to SEQ ID NO: 2, 3 or 4; and that contains a deletion of a polyadenylation site present in SEQ ID NO: 2, 3 or 4.

2. An isolated or purified polynucleotide that is at least 95% identical to SEQ ID NO: 2 and that contains the deletion of a polyadenylation site present in SEQ ID NO: 2.

3. An isolated or purified polynucleotide that is at least 95% identical to SEQ ID NO: 3 and that contains the deletion of a polyadenylation site present in SEQ ID NO: 3.

4. An isolated or purified polynucleotide that is at least 95% identical to SEQ ID NO: 4 and that contains the deletion of a polyadenylation site present in SEQ ID NO: 4.

5. An isolated or purified polynucleotide comprising the polynucleotide of claim 1 and further comprising a polynucleotide encoding a *Plasmodium* subtilisin-like maturase SUB2.

6. A vector comprising the isolated or purified polynucleotide of claim 1.

7. An isolated host cell comprising the isolated or purified polynucleotide of claim 1.

8. The host cell of claim 7 that is a *Plasmodium* host cell.

* * * * *